US010603279B2

(12) United States Patent
Giardiello et al.

(10) Patent No.: US 10,603,279 B2
(45) Date of Patent: Mar. 31, 2020

(54) COMPOSITIONS OF LOPINAVIR

(75) Inventors: Marco Norman Giardiello, Liverpool (GB); Thomas Oliver McDonald, Liverpool (GB); Andrew Owen, Liverpool (GB); Steven Paul Rannard, Liverpool (GB); Philip John Martin, Liverpool (GB); Darren Lee Smith, Liverpool (GB); James Long, Liverpool (GB)

(73) Assignee: The University of Liverpool, Liverpool (GB)

( * ) Notice: Subject to any disclaimer, the term of this patent is extended or adjusted under 35 U.S.C. 154(b) by 0 days.

(21) Appl. No.: 14/343,169

(22) PCT Filed: Sep. 7, 2012

(86) PCT No.: PCT/GB2012/052209
§ 371 (c)(1),
(2), (4) Date: Mar. 6, 2014

(87) PCT Pub. No.: WO2013/034926
PCT Pub. Date: Mar. 14, 2013

(65) Prior Publication Data
US 2014/0212501 A1  Jul. 31, 2014

(30) Foreign Application Priority Data
Sep. 9, 2011  (GB) .................... 1115634.6

(51) Int. Cl.
| | | |
|---|---|---|
| *A61K 31/513* | (2006.01) | |
| *A61K 9/16* | (2006.01) | |
| *A61K 9/14* | (2006.01) | |
| *A61K 9/51* | (2006.01) | |
| *A61K 9/19* | (2006.01) | |
| *A61K 45/06* | (2006.01) | |

(52) U.S. Cl.
CPC .............. *A61K 9/1682* (2013.01); *A61K 9/14* (2013.01); *A61K 9/19* (2013.01); *A61K 9/5138* (2013.01); *A61K 31/513* (2013.01); *A61K 45/06* (2013.01)

(58) Field of Classification Search
None
See application file for complete search history.

(56) References Cited

U.S. PATENT DOCUMENTS

| | | | | |
|---|---|---|---|---|
| 2003/0180352 | A1* | 9/2003 | Patel ..................... | A61K 9/1617 424/465 |
| 2003/0236236 | A1* | 12/2003 | Chen et al. ................. | 514/171 |
| 2006/0287542 | A1* | 12/2006 | von Corswant ..... | A61K 9/0019 554/108 |
| 2011/0236437 | A1* | 9/2011 | Destache ...................... | 424/400 |

FOREIGN PATENT DOCUMENTS

| | | |
|---|---|---|
| EP | 2279728 | 2/2011 |
| WO | WO2008/067164 | 6/2008 |
| WO | WO2009/118356 | 10/2009 |
| WO | WO2009/153654 | 12/2009 |
| WO | WO2010/068899 | 6/2010 |
| WO | WO2011/128623 | 10/2011 |

OTHER PUBLICATIONS

PCT Search Report and Written Opinion for PCT/GB2012/052209, completed Dec. 10, 2012.
United Kingdom Search Report and Written Opinion for 1115634.6, completed Jan. 5, 2012.
Wang et al., "Photolumunescence studies from ZNO nanorod arrays synthesized by hydrothermal method with Polyvinyl alcohol as surfactant", Materials Letters 62 (2008), pp. 2637-2639.
Shibata et al., "Polymeric nanoparticles containing combination antiretroviral drugs for HIV type 1 treatment", AIDS Research and Human Retroviruses, vol. 29, No. 5, 2015, pp. 746-754.
Angshuman et al., "Alginate Based Nanoparticulate Drug Delivery for Anti HIV Drug Lopinavir", Journal of Global Pharma Technology, 2010; 2(3): 126-132.
Destache et al., "Antiretroviral release from poly(DL-lactide-co-glycolide) nanoparticles in mice", Journal of Antimicrobial Chemotherapy, 2010: 65: 2183-2187.
Parikh et al., "Simultaneous Determination of Ketoconazole, Ritonavir and Lopinavir in Solid Lipid Nanoparticles by RP-LC", Chromatographia 2010, 71 May (No. 9/10), pp. 941-946.
McDonald et al., "Antiretroviral Solid Drug Nanoparticles with Enhanced Oral Bioavailability: Production, Characterization, and In Vitro-In Vivo Correlation," Adv. Healthcare Mater., 2014, 3, pp. 400-411.

(Continued)

*Primary Examiner* — Patricia Duffy
*Assistant Examiner* — Garen Gotfredson
(74) *Attorney, Agent, or Firm* — Barnes & Thornburg LLP

(57) ABSTRACT

The present invention relates to a solid composition and an aqueous dispersion comprising nanoparticles of the antiretroviral drug lopinavir. The solid composition and aqueous dispersion additionally comprise a mixture of a hydrophilic polymer and a surfactant. The surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof. The hydrophilic polymer is suitably selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof. The present invention also relates to processes for preparing both the solid composition and the aqueous dispersion, as well as to their use in therapy for the treatment and/or prevention of retroviral infections such as human immunodeficiency virus (HIV).

10 Claims, 11 Drawing Sheets

(56) References Cited

OTHER PUBLICATIONS

Giardiello et al., "Accelerated oral nanomedicine discovery from miniaturized screening to clinical production exemplified by paediatric HIV nanotherapies," Nature Communications, DOI: 10.1038/ncomms13184.

* cited by examiner

COMPOSITIONS OF LOPINAVIR

CROSS-REFERENCE TO RELATED APPLICATIONS

This application is a national stage entry under 35 USC § 371(b) of PCT International Application No. PCT/GB2012/052209, filed Sep. 7, 2012, which claims priority to United Kingdom Patent Application No. 1115634.6, filed Sep. 9, 2011, the entire disclosures of all of which are incorporated herein by reference.

The present invention relates to compositions of the anti-HIV drug lopinavir that are suitable for pharmaceutical use. More specifically, the present invention relates to a solid composition of lopinavir and, in another aspect, to an aqueous dispersion of lopinavir. The present invention also relates to processes for preparing both the solid composition and the aqueous dispersion, as well as to their use in therapy for the treatment and/or prevention of retroviral infections such as human immunodeficiency virus (HIV).

BACKGROUND OF THE INVENTION

Human Immunodeficiency Virus (HIV) is a major cause of morbidity and mortality in both the developed and the developing world. HIV is a retrovirus that causes acquired immunodeficiency syndrome (AIDS) in humans, which in turn allows life-threatening infections and cancers to thrive as the immune system progressively fails.

HIV infection typically occurs through the transfer of bodily fluids, such as blood, semen, vaginal fluid, pre-ejaculate, or breast milk, from one individual to another. HIV may be present within these bodily fluids as either the free virus, or as a virus present within infected immune cells. HIV-1 tends to be the most virulent form of HIV, and is transmitted as a single-stranded enveloped RNA virus which, upon entry into a target cell, is converted into double-stranded DNA by reverse transcription. This DNA may then become integrated into the host's DNA where it can reside in a latent from and avoid detection by the immune system. Alternatively, this DNA may be re-transcribed into RNA genomes and translated to form viral proteins that are released from cells as new virus particles, which can then spread further.

A drug commonly used in the treatment of HIV, and particularly HIV-1, is the protease inhibitor lopinavir (LPV). Lopinavir is sold commercially as either film coated tablets or an oral solution both under the trade name Kaletra®. Both forms of Kaletra® are combination therapies which comprise Ritonavir in addition to Lopinavir. Ritonavir functions as a cytochrome P450 isoform 3A4 (CYP3A4) inhibitor to decrease the hepatic clearance of lopinavir.

The structure of lopinavir is shown below.

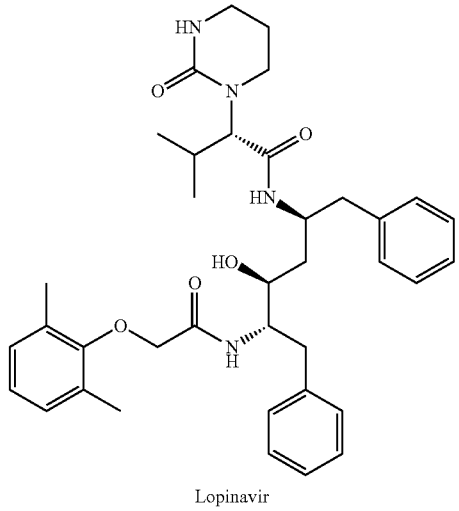 [SMILES: Cc1cccc(C)c1OCC(=O)N[C@@H](Cc1ccccc1)[C@@H](O)C[C@H](Cc1ccccc1)NC(=O)[C@H](C(C)C)N1CCCNC1=O]

Lopinavir

Although lopinavir is effective in prolonging life expectancy in HIV sufferers, there area number of drawbacks associated with the currently available formulations of lopinavir.

Lopinavir acts on an intracellular target, so the ability of lopinavir to penetrate into and accumulate within cells is a prerequisite for effective treatment (Owen and Khoo, *Journal of HIV Therapy*, 2004, 9(4), 53-57). One particular problem with the current formulations of lopinavir is that the penetration of the drug into cells is variable and inadequate both within and between patients. As cellular penetration and accumulation of the drug is necessary in order to effectively treat the HIV infected cells, there is a need for formulations of lopinavir that exhibit good levels of cellular accumulation, particularly in immune cells (e.g. macrophages and CD4+ lymphocytes).

In addition, the distribution of lopinavir throughout the body is also not uniform with current lopinavir formulations, and certain target tissues and sanctuary sites, such as the brain and the testis, can suffer from poor exposure to the drug. This can lead to sub-therapeutic levels of the drug reaching certain tissues, with the consequential effect that HIV infected cells residing in these tissues may not be adequately treated. Furthermore, resistance to lopinavir is becoming an increasing problem (Delaugerre et al., *Antimicrob Agents Chemother.* 2009, 53(7); 2934-2939), and exposure to sub-therapeutic levels of lopinavir in these tissues increases the risk that lopinavir-resistant strains of HIV can arise and reseed the blood. Resistant strains of HIV are also transmittable meaning that individuals can be newly infected with resistant virus. There is, therefore, a need for formulations that provide an improved distribution of lopinavir throughout the body, and in particular to sanctuary sites for the virus.

A further problem with current lopinavir formulations is that it is necessary to administer large doses of the drug each day (typically the adult dose is 800 mg twice a day), along with multiple other anti-HIV drugs. As a consequence, a patient will need to consume a large tablet or capsule of lopinavir, or multiple smaller dosage tablets or capsules, in order to obtain the required dosage. This can inevitably lead to problems with patient compliance. Furthermore, lopinavir treatment is also associated with a number of adverse side effects, which represent a major problem for patients, especially over prolonged periods (Perez-Molina et al., *J Anti-* microb Chemother., 2008, 62(2), 234-245). For these reasons, there is a need for more effective formulations of lopinavir, which in turn may enable the required dosage of lopinavir to be lowered. Lower doses could have an effect on the number and/or size of the tablets/capsules that need to be consumed by the patient, as well as prevalence of the adverse side effects.

There is also a need for dosage forms that permit the dosage to be easily varied on a patient-by-patient basis depending on factors such as the age (including paediatric dosing) and weight of the patient, as well as the severity and stage of the infection.

It is therefore an object of the present invention to provide improved formulations of lopinavir that address one or more of the drawbacks associated with the current lopinavir formulations.

In particular, it is an object of the invention is to provide lopinavir formulations exhibiting good cell penetration and a more optimum and effective distribution throughout the body.

Another object of the present invention is to provide lopinavir formulations with a high drug loading.

Another object of the present invention is to provide lopinavir formulations which permits lower overall dosage of lopinavir in HIV treatments.

SUMMARY OF THE INVENTION

According to a first aspect of the present invention there is provided a solid lopinavir composition, comprising nanoparticles of lopinavir dispersed within a mixture of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

According to a second aspect of the present invention there is provided an aqueous dispersion, comprising a plurality of nanoparticles dispersed in an aqueous medium, the nanoparticles comprising a core of lopinavir and a coating of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

Both the solid lopinavir composition and the aqueous dispersion of the present invention comprise the lopinavir drug substance in a nanoparticulate form. The lopinavir nanoparticles of the present invention provide improved dosage forms of lopinavir, particularly with respect to stability and efficacy. The solid lopinavir composition and the aqueous dispersion of the present invention also provide good cell penetration and accumulation, especially in immune cells. In certain embodiments, the level of cell penetration is significantly improved relative to conventional lopinavir formulations. The solid lopinavir composition and the aqueous dispersion of the present invention also provide an improved distribution of drug throughout the body and provide higher drug levels in certain target tissues such as the testes and brain. These advantages provide the opportunity for a more effective treatment of HIV and may also enable the required dosage of lopinavir to be reduced.

The nanoparticles of lopinavir also possess low cytotoxicity and compositions with high drug loadings can be prepared.

The provision of nanoparticles in a solid composition can also be advantageous because it provides a more stable form of the drug that is suitable for long term storage. Furthermore, the solid composition can be consumed as a solid dosage form when required in certain embodiments of the invention, or, alternatively, they can be dispersed in a suitable aqueous diluent when required to form an aqueous dispersion of the nanoparticles for administration.

Furthermore, the solid compositions of the present invention allow for higher drug loadings than known lopinavir formulations, which enables excipient dosages (e.g. surfactants) and the size of the dosage form to be reduced.

Finally, the solid compositions of the present invention are ideally suited to personalised medicine regimes, because the solid compositions are substantially homogeneous, meaning that partial doses may be accurately measured. Furthermore, the solid compositions of the present invention are readily dispersible within an aqueous medium to provide stable aqueous dispersions. Such stable aqueous dispersions can themselves be partitioned in a pre-determined manner to provide an accurate liquid dose of lopinavir. Such methods of providing personalised doses are particularly applicable to paediatric administration, since children require lower doses of lopinavir. Moreover, lopinavir doses can be accordingly adapted to suit a patient's weight, age, and other circumstances (such as the stage or severity of the HIV infection).

According to a third aspect of the invention, there is provided an aqueous dispersion, obtainable by, obtained by, or directly obtained by dispersing the solid composition of the first aspect in an aqueous medium.

According to a fourth aspect of the present invention there are provided processes for the preparation of a solid composition as defined herein.

According to a fifth aspect of the present invention, there is provided a solid composition obtainable by, obtained by, or directly obtained by the process according to the fourth aspect.

According to a sixth aspect of the present invention, there is provided a pharmaceutical composition comprising a solid composition of the first or fifth aspects of the invention, or an aqueous dispersion of the second or third aspects of the invention, and optionally a further pharmaceutically acceptable diluent, carrier, or excipient.

According to a seventh aspect of the present invention, there is provided a solid composition or an aqueous dispersion as defined herein for use as a medicament.

According to a eighth aspect of the present invention, there is provided a solid composition or an aqueous dispersion as defined herein for use in the treatment and/or prevention of retroviral infections (e.g. HIV).

According to a ninth aspect of the present invention, there is provided a use of a solid composition or an aqueous dispersion as defined herein in the manufacture of a medicament for use in the treatment and/or prevention of retroviral infections (e.g. HIV).

According to a tenth aspect of the present invention, there is provided a method of treating and/or preventing a retroviral infection (e.g. HIV), comprising administering a therapeutically effective amount of a solid composition, an aqueous dispersion, or a pharmaceutical composition as defined herein to a patient suffering from or at risk of suffering from the retroviral infection.

According to an eleventh aspect of the present invention there is provided a kit of parts comprising a solid composition as defined herein or pharmaceutical composition comprising the solid composition as defined herein, and a pharmaceutically acceptable diluent.

Features, including optional, suitable and preferred features of any aspect of the invention are, unless otherwise stated, also features, including optional, suitable and preferred features of any other aspect of the invention.

BRIEF DESCRIPTION OF THE FIGURES

In the Example section reference is made to the following figures:

FIG. 5A shows time course measurements made upon nanodispersions of the cold PVA/Vit-E samples (for both 5% and 10% surfactant samples) with respect to their (a) z-average particle size (nm); (b) particle size polydispersity; and (c) average zeta potential (mV), each for PVA/Vit-E samples comprising both 5% (left hand side) and 10% (right hand size) surfactant content. FIG. 5B shows time course measurements made upon nanodispersions of the cold PVA/T-20 samples (for both 5% and 10% surfactant samples) with respect to their (a) z-average particle size (nm); (b) particle size polydispersity; and (c) average zeta potential (mV), each for PVA/T-20 samples comprising both 5% (left hand side) and 10% (right hand size) surfactant content. FIG. 5C shows time course measurements made upon nanodispersions of the cold PVA/NDC samples (for both 5% and 10% surfactant samples) with respect to their (a) z-average particle size (nm); (b) particle size polydispersity; and (c) average zeta potential (mV), each for PVA/NDC samples comprising both 5% (left hand side) and 10% (right hand size) surfactant content.

DETAILED DESCRIPTION OF THE INVENTION

Definitions

Figure 1:
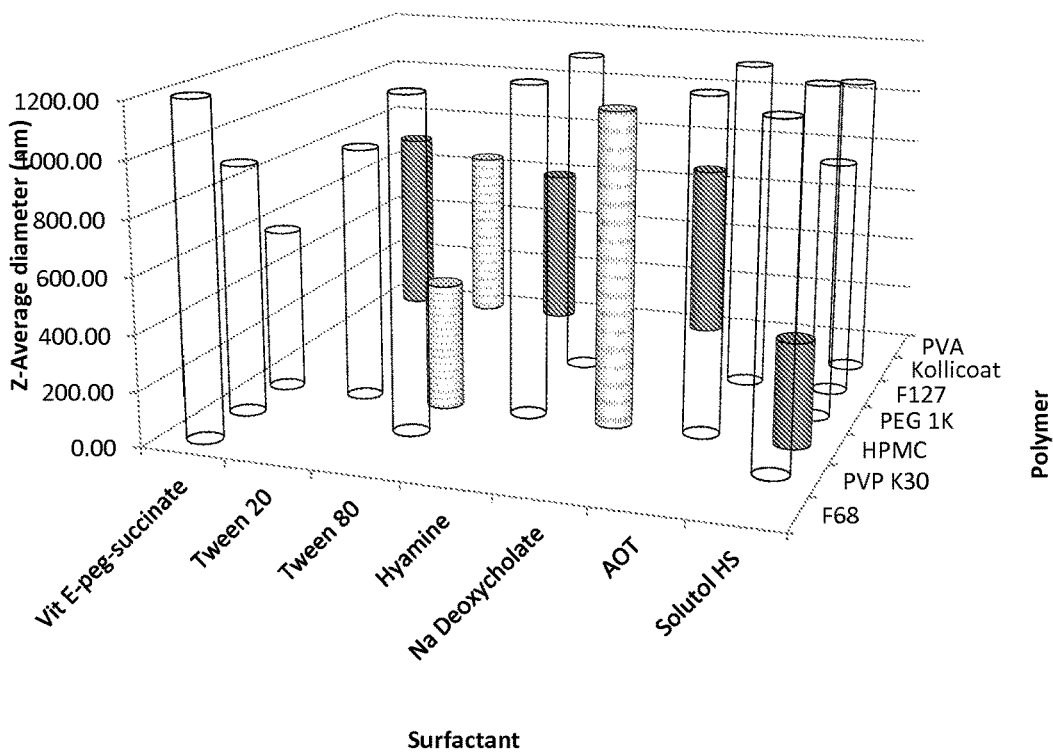
FIG. 1 shows a 3-D bar chart representing the results from the study described in Example 4 herein, where clear "hits" (i.e. compositions satisfying the nanodispersion assessment criteria—see Example 1) are shown as grey bars, near misses are shown as while bars with dots, more distant misses are shown as transparent bars, and non-hits are shown without bars. The z-average particle size for each of the hits, near misses, and more distant misses is given on the vertical axis.

The term "nanoparticle" or "nanoparticulate" is used herein to mean a particle having a size of less than or equal to 1 micron (μm).

The term "lopinavir" is used herein to refer to lopinavir, commonly used in HIV treatments, and includes pharmaceutically acceptable salts and solvates thereof, as well as any polymorphic or amorphous forms thereof.

It is to be appreciated that references to "preventing" or "prevention" relate to prophylactic treatment and includes preventing or delaying the appearance of clinical symptoms of the state, disorder or condition developing in a human that may be afflicted with or predisposed to the state, disorder or condition but does not yet experience or display clinical or subclinical symptoms of the state, disorder or condition.

It will be appreciated that references to "treatment" or "treating" of a state, disorder or condition includes: (1) inhibiting the state, disorder or condition, i.e., arresting, reducing or delaying the development of the disease or a relapse thereof (in case of maintenance treatment) or at least one clinical or subclinical symptom thereof, or (2) relieving or attenuating the disease, i.e. causing regression of the state, disorder or condition or at least one of its clinical or subclinical symptoms.

A "therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the patient to be treated.

Solid Liponavir Composition

The present invention provides a solid lopinavir composition, comprising nanoparticles of lopinavir dispersed within a mixture of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

The nanoparticles of lopinavir drug substance are dispersed within a solid excipient mixture comprising the hydrophilic polymer and the surfactant.

The solid composition of the present invention may be administered as it is to a patient, or further formulated to provide a pharmaceutical composition in the form of, for example, a tablet, capsule, lozenge, or a dispersible powder or granule formulation.

The nanoparticles of lopinavir have an average particle size of less than or equal to 1 micron (μm). In a particular embodiment, the nanoparticles of lopinavir have an average particle size of between 100 and 1000 nm. In another embodiment, the nanoparticles of lopinavir have an average particle size between 100 and 800 nm. In another embodiment, the nanoparticles of lopinavir have an average particle size between 100 and 700 nm. In yet another embodiment, the nanoparticles of lopinavir have an average particle size between 100 and 600 nm.

The particle size of the nanoparticles may be assessed by any suitable technique known in the art (e.g. laser diffraction, laser scattering, electron microscopy). In an embodiment of the invention, particle size is assessed by dispersing the solid composition in an aqueous medium and determining the particle size with a Zetasizer (Malvern Instruments Ltd).

In an embodiment, the polydispersity of the nanoparticles of lopinavir is less than or equal to 0.8, suitably less than or equal to 0.6, and most suitably less than or equal to 0.5. The polydispersity relates to the size of the lopinavir nanoparticles and may be determined by suitable techniques known in the art (e.g. laser diffraction, laser scattering, electron microscopy). In an embodiment of the present invention, the polydispersity of particle sizes of the nanoparticles of lopinavir may be suitably assessed with a Malvern Zetasizer (Malvern Instruments Ltd).

In a particular embodiment, the average zeta potential of the nanoparticles of lopinavir when dispersed in an aqueous medium is between −100 and +100 mV. In another embodiment, the zeta potential of the nanoparticles of lopinavir is between −25 and +25 mV. In another embodiment, the zeta potential of the nanoparticles of lopinavir is between −20 and +20 mV. In yet another embodiment, the zeta potential of the nanoparticles of lopinavir is between −25 and 0 mV. In general it has been found that zeta potentials of a relatively small magnitude (either positive or negative) allow the nanoparticles to better penetrate into and accumulate within cells. In accordance with the present invention, average zeta potentials can be measured by techniques known in the art, such as using a Zetasizer (Malvern Instruments Ltd).

The solid composition may comprise particles or granules of larger size, for example, 5 to 30 microns (μm) in size, but each particle or granule contain a plurality of nanoparticles of lopinavir dispersed within a mixture of the hydrophilic polymer and surfactant. Furthermore, these larger particles or granules disperse when the solid composition is mixed with an aqueous medium to form discrete nanoparticles of lopinavir.

In an embodiment, the solid composition comprises a single hydrophilic polymer and a single surfactant selected from those listed herein. In an alternative embodiment, the solid composition comprises two or more hydrophilic polymers and/or two or more surfactant selected from those listed herein may be present.

Hydrophilic Polymer

A wide range of hydrophilic polymers are suitable for use in pharmaceutical formulations. Examples of such polymers include:

(a) homo or co-polymers of monomers selected from: vinyl alcohol, acrylic acid, methacrylic acid, acrylamide, methacrylamide, acrylamide aminoalkylacrylates, aminoalkylmethacrylates, hydroxyethylacrylate, methylpropane sulphonates, hydroxyethylmethylacrylate, vinyl pyrrolidone, vinyl imidazole, vinyl amines, vinyl pyridine, ethyleneglycol, propylene glycol, ethylene oxides, propylene oxides, ethyleneimine, styrenesulphonates, ethyleneglycolacrylates and ethyleneglycol methacrylate;

(b) polyvinyl alcohol (PVA), a polyvinyl alcohol-polyethylene glycol graft copolymer, a block copolymer of polyoxyethylene and polyoxypropylene, polyethylene glycol, and polyvinylpyrrolidone, or a combination thereof (c) cellulose derivatives for example cellulose acetate, methylcellulose, methyl-ethylcellulose, hydroxy-ethylcellulose, hydroxy-ethylmethyl-cellulose, hydroxy-propylcellulose (HPC), hydroxy-propylmethylcellulose (HPMC), hydroxypropylbutylcellulose, ethylhydroxy-ethylcellulose, carboxymethylcellulose and its salts (eg the sodium salt—SCMC), or carboxy-methylhydroxyethylcellulose and its salts (for example the sodium salt)

(d) gums such as guar gum, alginate, locust bean gum and xanthan gum (e) polysaccharides such as dextran, xyloglucan and gelatin (or hydrolysed gelatin);

(f) cyclodextrins such as beta-cyclodextrin;

(g) mixtures thereof.

Copolymers may be statistical copolymers (also known as a random copolymer), a block copolymer, a graft copolymer or a hyperbranched copolymer. Additional co-monomers may also be present provided that their presence does not effect the water-solubility of the resulting polymeric material.

Particular examples of homopolymers include poly-vinyl-alcohol (PVA), poly-acrylic acid, poly-methacrylic acid, poly-acrylamides (such as poly-N-isopropylacrylamide), poly-methacrylamide; poly-acrylamines, poly-methyl-acrylamines, (such as polydimethylaminoethylmethacrylate and poly-N-morpholinoethylmethacrylate), polyvinylpyrrolidone (PVP), poly-styrenesulphonate, polyvinylimidazole, polyvinylpyridine, poly-2-ethyl-oxazoline poly-ethyleneimine and ethoxylated derivatives thereof.

In the present invention, the hydrophilic polymer is selected from those hydrophilic polymers that are capable of stabilising nanoparticles of lopinavir in an aqueous dispersion together with a surfactant as defined herein, and which are also suitable for pharmaceutical use (e.g. they are approved for use by the US Food and Drug Administration).

The hydrophilic polymer is therefore suitably selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof.

The hydrophilic polymer is a pharmaceutically acceptable hydrophilic polymer.

It shall be appreciated that any molecular weight (Mw) or molecular number (Mn) values quoted herein span the range of Mw and Mn values that may be present in the polymer.

In a particular embodiment, the polyvinyl alcohol has an average molecular weight between 5000 and 200000 Da, suitably with a 75-90% hydrolysis level (i.e. % free hydroxyls). In a particular embodiment, the polyvinyl alcohol has a 75-90% hydrolysis level. In another embodiment, the polyvinyl alcohol has a 75-85% hydrolysis level. In a particular embodiment, the polyvinyl alcohol has an average molecular weight between 9000 and 10000 Da, suitably with an 80% hydrolysis level. In a particular embodiment, the polyvinyl alcohol has a 75-90% hydrolysis level, suitably a 75-85% hydrolysis level.

In a particular embodiment, the polyvinyl alcohol-polyethylene glycol graft copolymer has an average molecular weight between 30000 and 60000 Da, suitably with a PVA/PEG ratio of between 90:10 and 25:75. In a particular embodiment, the polyvinyl alcohol-polyethylene glycol graft copolymer has an average molecular weight between 40000 and 50000 Da, suitably with a PVA/PEG ratio of between 85:15 and 25:75. Suitably the polyvinyl alcohol-polyethylene glycol graft copolymer has a PVA/PEG ratio of between 90:10 and 25:75, more suitably a PVA/PEG ratio of between 85:15 and 25:75. In a particular embodiment, the polyvinyl alcohol-polyethylene glycol graft copolymer is a Kollicoat® polymer (supplied by BASF). In a particular embodiment, the Kollicoat® is Kollicoat® Protect.

The block copolymer of polyoxyethylene and polyoxypropylene is suitably either a diblock copolymer of polyoxyethylene and polyoxypropylene or a triblock copolymer thereof. In a particular embodiment, the block copolymer of polyoxyethylene and polyoxypropylene is a Poloxamer.

A "poloxamer" is a non-ionic triblock copolymer comprising a central hydrophobic chain of polyoxypropylene, and hydrophilic chains of polyoxyethylene either side of this central hydrophobic chain. A "poloxamer" is typically named with the letter "P" followed by three numerical digits (e.g. P407), where the first two digits multiplied by 100 gives the approximate molecular mass of the polyoxypropylene chain, and the third digit multiplied by 10 provides the percentage polyoxyethylene content of the poloxamer. For example, P407 is a poloxamer having a polyoxypropylene molecular mass of about 4,000 g/mol and a polyoxyethylene content of about 70%. Poloxamers are also known as Pluronics®, as well as by several other commercial names.

The Poloxamer is suitably a pharmaceutically acceptable Poloxomer. In a particular embodiment, the poloxamer is Poloxamer P407 or Poloxamer P188.

In a particular embodiment, the polyethylene glycol (PEG) has an average molecular weight of 500 to 20000 Da. In a particular embodiment, the polyethylene glycol is PEG 1K (i.e. with an average molecular weight of about 1000 Da).

In a particular embodiment, the HPMC has an average molecular weight of 10000 to 400000 Da. In a particular embodiment, the HPMC has an average molecular weight of about 10000.

In a particular embodiment, the polyvinylpyrrolidone has an average molecular weight of 2000 to 1,000,000 Da. In a particular embodiment, the polyvinylpyrrolidone has an average molecular weight of 30000 to 55000 Da. In a particular embodiment the polyvinylpyrrolidone is polyvinylpyrrolidone K30 (PVP K30).

In a particular embodiment, the hydrophilic polymer is selected from PVA, a Kollicoat®, Poloxamer 407, PEG 1K, HPMC, PVP K30, and Poloxamer 188, or a combination thereof.

In a particular embodiment, the hydrophilic polymer is selected from PVA or HPMC.

In a particular embodiment, the hydrophilic polymer is PVA.

Surfactant

Surfactants suitable for pharmaceutical use may be:
non-ionic (e.g. ethoxylated triglycerides; fatty alcohol ethoxylates; alkylphenol ethoxylates; fatty acid ethoxylates; fatty amide ethoxylates; fatty amine ethoxylates; sorbitan alkanoates; ethylated sorbitan alkanoates; alkyl ethoxylates; Pluronics™; alkyl polyglucosides; stearol ethoxylates; alkyl polyglycosides; sucrose fatty acid esters, anionic, cationic, amphoteric or zwitterionic);
anionic (e.g. alkylether sulfates; alkylether carboxylates; alkylbenzene sulfonates; alkylether phosphates; dialkyl sulfosuccinates; sarcosinates; alkyl sulfonates; soaps; alkyl sulfates; alkyl carboxylates; alkyl phosphates; paraffin sulfonates; secondary n-alkane sulfonates; alpha-olefin sulfonates; isethionate sulfonates; alginates);
cationic (e.g. fatty amine salts; fatty diamine salts; quaternary ammonium compounds; phosphonium surfactants; sulfonium surfactants; sulfonxonium surfactants); or
zwitterionic (e.g. N-alkyl derivatives of amino acids (such as glycine, betaine, aminopropionic acid); imidazoline surfactants; amine oxides; amidobetaines).

Alkoxylated nonionic's (especially the PEG/PPG Pluronic™ materials), phenol-ethoxylates (especially TRITON™ materials), alkyl sulphonates (especially SDS), ester surfactants (preferably sorbitan esters of the Span™ and Tween™ types) and cationics (especially cetyltrimethylammonium bromide—CTAB) are particularly suitable as surfactants.

In the present invention, the surfactant is suitably selected from those surfactants that are capable of stabilising nanoparticles of lopinavir together with a hydrophilic polymer as defined herein, and which are also approved for pharmaceutical use (e.g. they are approved for use by the US Food and Drug Administration).

The surfactant is therefore suitably selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

It will be appreciated that the hydrophilic polymer and the surfactant may both be either PVA or a block copolymer of polyoxyethylene and polyoxypropylene. In other words, the PVA and block copolymer of polyoxyethylene and polyoxypropylene may function as both the surfactant and the hydrophilic polymer. The total amount of PVA or block copolymer of polyoxyethylene and polyoxypropylene that may be present in such circumstances is that defined hereinafter for the total of the surfactant and hydrophilic polymer.

In a particular embodiment, the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, and polyethyleneglycol-12-hydroxystearate, or a combination thereof.

In a particular embodiment, the vitamin-E-polyethylene glycol-succinate (Vit-E-PEG-succinate) has a PEG moiety with an average molecular weight of 500 to 10000 Da. In a particular embodiment, the vitamin-E-polyethylene glycol-succinate (Vit-E-PEG-succinate) has a PEG portion with an average molecular weight of about 1000 Da (which is commercially available as Tocofersolan).

In a particular embodiment, the polyoxyethylene sorbitan fatty acid ester is selected from Polysorbate 20 (commercially available as Tween® 20) and Polysorbate 80 (commercially available as Tween® 80).

In a particular embodiment, the polyethylenglycol-12-hydroxystearate has a molecular weight of 300 to 3000 Da. In a particular embodiment, the polyethylenglycol-12-hydroxystearate has a molecular weight of 600 to 700 Da (e.g. commercially available as Solutol® HS).

In a particular embodiment, the surfactant is selected from vitamin-E-polyethylene glycol-succinate (Vit-E-PEG-succinate), a polyoxyethylene sorbitan fatty acid ester, sodium deoxycholate, polyethyleneglycol-12-hydroxystearate, or a combination thereof.

In a particular embodiment, the surfactant is selected from vitamin-E-polyethylene glycol-succinate (Vit-E-PEG-succinate), Polysorbate 20, Polysorbate 80, sodium deoxycholate, or polyethyleneglycol-12-hydroxystearate.

In a particular embodiment, the surfactant is selected from vitamin-E-polyethylene glycol-succinate (Vit-E-PEG-succinate), Polysorbate 20, Polysorbate 80, or sodium deoxycholate.

In a particular embodiment, the surfactant is selected from vitamin-E-polyethylene glycol-succinate (Vit-E-PEG-succinate), Polysorbate 20, or sodium deoxycholate.

In a particular embodiment, the surfactant is vitamin-E-polyethylene glycol-succinate (Vit-E-PEG-succinate).

Particular Combinations of Hydrophilic Polymer and Surfactant

PVA is a particularly suitable hydrophilic polymer where the surfactant is selected from vitamin-E-polyethylene glycol-succinate (Vit-E-PEG-succinate), a polyoxyethylene sorbitan fatty acid ester, and sodium deoxycholate.

PVA is a particularly suitable hydrophilic polymer where the surfactant is selected from vitamin-E-polyethylene glycol-succinate (Vit-E-PEG-succinate), Polysorbate 20, Polysorbate 80, and sodium deoxycholate.

PVA is a particularly suitable hydrophilic polymer where the surfactant is selected from vitamin-E-polyethylene glycol-succinate (Vit-E-PEG-succinate), Polysorbate 20, and sodium deoxycholate.

PVA is a particularly suitable hydrophilic polymer where the surfactant is vitamin-E-polyethylene glycol-succinate (Vit-E-PEG-succinate).

The above PVA combinations are particularly advantageous where the PVA has an average molecular weight between 9000 and 10000 Da, suitably with a 75-85% hydrolysis level.

HPMC is a particularly suitable hydrophilic polymer where the surfactant is a polyoxyethylene sorbitan fatty acid ester, sodium deoxycholate, or polyethyleneglycol-12-hydroxystearate.

HPMC is a particularly suitable hydrophilic polymer where the surfactant is a polyoxyethylene sorbitan fatty acid ester, or polyethyleneglycol-12-hydroxystearate.

HPMC is a particularly suitable hydrophilic polymer where the surfactant is Polysorbate 80, or polyethyleneglycol-12-hydroxystearate.

HPMC is a particularly suitable hydrophilic polymer where the surfactant is polyethyleneglycol-12-hydroxystearate (e.g. as per Solutol® HS).

Formulation of Solid Composition

In a particular embodiment, the solid composition as defined herein comprises 40 to 90 wt % of lopinavir. In another embodiment, the solid composition comprises 50 to 75 wt % of lopinavir. In another embodiment, the solid composition comprises 60 to 70 wt % of lopinavir.

The solid compositions of the present invention therefore permit high drug loadings, which keeps the potentially toxic excipients (e.g. surfactants) to a minimum.

Suitably, the solid composition comprises 10 to 60 wt % of the hydrophilic polymer and surfactant combined, more suitably 20 to 60 wt %, even more suitably 25 to 50 wt %, most suitably 25 to 40 wt %. In a particular embodiment, the solid composition comprises 25 to 35 wt % of the hydrophilic polymer and surfactant combined.

In a particular embodiment, the solid composition comprises 5 to 50 wt % of hydrophilic polymer. In another embodiment, the solid composition comprises 10 to 40 wt % of hydrophilic polymer. In another embodiment, the solid composition comprises 15 to 30 wt % of hydrophilic polymer. In a particular embodiment, the solid composition comprises 15 to 25 wt % of hydrophilic polymer.

In a particular embodiment, the solid composition comprises 1 to 25 wt % of surfactant. In another embodiment, the solid composition comprises 2 to 20 wt % of surfactant. In another embodiment, the solid composition comprises 3 to 10 wt % of surfactant.

Where either PVA or the block copolymer of polyoxyethylene and polyoxypropylene serve both as the surfactant and the hydrophilic polymer, the abovementioned wt % values for the hydrophilic polymer and surfactant combined still apply. For example, where either PVA or the block copolymer of polyoxyethylene and polyoxypropylene serve both as the surfactant and the hydrophilic polymer, the solid composition suitably comprises 10 to 60 wt % of PVA or a block copolymer of polyoxyethylene and polyoxypropylene; more suitably 20 to 60 wt % of PVA or a block copolymer of polyoxyethylene and polyoxypropylene, even more suitably 25 to 50 wt % of PVA or a block copolymer of polyoxyethylene and polyoxypropylene, most suitably 25 to 40 wt % of PVA or a block copolymer of polyoxyethylene and polyoxypropylene. In a particular embodiment, the solid composition comprises 25 to 35 wt % of PVA or a block copolymer of polyoxyethylene and polyoxypropylene.

In an embodiment, the solid composition comprises the hydrophilic polymer and surfactant in a respective ratio of between 30:1 and 1:10. In a particular embodiment, the solid composition comprises the hydrophilic polymer and surfactant in a respective ratio of between 15:1 and 1:2. In another embodiment, the solid composition comprises the hydrophilic polymer and surfactant in a respective ratio of between 10:1 and 2:1. In a particular embodiment, the solid composition comprises the hydrophilic polymer and surfactant in a respective ratio of between 6:1 and 3:1.

In a particular embodiment, the solid composition comprises:
  40 to 80 wt % lopinavir;
  10 to 40 wt % hydrophilic polymer; and
  2 to 20 wt % surfactant.

In a particular embodiment, the solid composition comprises 1-29 wt % PVA as the hydrophilic polymer, and 1-24 wt % vitamin-E-polyethylene glycol-succinate (Vit-E-PEG-succinate) as the surfactant.

In a particular embodiment, the solid composition comprises 15-25 wt % PVA as the hydrophilic polymer, and 5-15 wt % vitamin-E-polyethylene glycol-succinate (Vit-E-PEG-succinate) as the surfactant. In another embodiment, the solid composition comprises 20-25 wt % PVA as the hydrophilic polymer, and 5-10 wt % vitamin-E-polyethylene glycol-succinate (Vit-E-PEG-succinate) as the surfactant. In a particularly preferred embodiment, the solid composition comprises 18-22 wt % PVA as the hydrophilic polymer, and 8-12 wt % vitamin-E-polyethylene glycol-succinate (Vit-E-PEG-succinate) as the surfactant. Suitably, such compositions comprise 25 to 35 wt % of the hydrophilic polymer and surfactant combined, more suitably 28 to 32 wt %. In such embodiments, the solid composition suitably comprises nanoparticles of lopinavir having an average particle size between 500 and 650 nm, and an average zeta potential when dispersed in an aqueous medium between −5 mV and −15 mV.

In a particular embodiment, the solid composition comprises 1-29 wt % PVA as the hydrophilic polymer, and 1-24 wt % Polysorbate 20 (e.g. Tween® 20) as the surfactant. Suitably such a composition comprises 25 to 35 wt % of the hydrophilic polymer and surfactant combined.

In a particular embodiment, the solid composition comprises 5-14 wt % PVA as the hydrophilic polymer, and 16-25 wt % Polysorbate 80 (e.g. Tween® 80) as the surfactant. Suitably such a composition comprises 25 to 35 wt % of the hydrophilic polymer and surfactant combined.

In a particular embodiment, the solid composition comprises 11-29 wt % PVA as the hydrophilic polymer, and 1-19 wt % sodium deoxycholate as the surfactant. Suitably such a composition comprises 25 to 35 wt % of the hydrophilic polymer and surfactant combined.

In a particular embodiment, the solid composition comprises 11-29 wt % HPMC as the hydrophilic polymer, and 1-19 wt % sodium deoxycholate as the surfactant. Suitably such a composition comprises 25 to 35 wt % of the hydrophilic polymer and surfactant combined.

In a particular embodiment, the solid composition comprises 16-24 wt % HPMC as the hydrophilic polymer, and 6-14 wt % polyethyleneglycol-12-hydroxystearate as the surfactant. Suitably such a composition comprises 25 to 35 wt % of the hydrophilic polymer and surfactant combined.

Unless otherwise stated, the above weight percentages relate to the % by weight of a particular constituent as a proportion of the total weight of the solid composition.

The solid composition may comprise one or more additional excipients, for instance, to further facilitate dispersion or stabilisation of dispersions of the nanoparticles either in a pharmaceutically acceptable diluent or in vivo.

Processes for Preparing the Solid Composition

Solid compositions of the present invention may be prepared by a number of methods well known in the art. Suitable techniques for forming such compositions are described in general terms in Horn and Reiger, *Angew. Chem. Int. Ed.*, 2001, 40, 4330-4361.

For example, the solid composition may be prepared by milling a solid form of lopinavir. The milling may occur in the presence of the hydrophilic polymer and surfactant, or, alternatively, they may be mixed with the milled drug after the milling step.

However, it is generally preferred that the solid lopinavir compositions of the present invention are prepared by an oil in water emulsion technique whereby the lopinavir is dissolved in the oil phase and the hydrophilic polymer and surfactant are present in the water phase. The oil and water solvents are then removed by freeze drying, spray drying or spray granulation to provide a solid composition according to the invention.

Thus, in accordance with the present invention, there is provided a process for preparing a solid composition as defined herein, the process comprising:
  (a) preparing an oil in water emulsion comprising:
    an oil phase comprising lopinavir; and
    an aqueous phase comprising a hydrophilic polymer and a surfactant, each as defined herein; and
  (b) removing the oil and water to form the solid composition.

An advantage of the process of the present invention is that the emulsions formed in step (a) are sufficiently homogenous and stable to allow for effective and uniform drying in step (b). Furthermore, the nanoparticles formed are substantially uniform in their physical form (size, shape etc.).

Step (a) may be performed by methods well-known in the art. Any suitable method for forming the oil in water emulsion defined in step (a) may therefore be used. In particular, the mixing of the oil and water phases to form the oil in water emulsion may be performed by methods well known in the art. For example, the mixing may involve stirring, sonication, homogenisation, or a combination thereof. In a particular embodiment, the mixing is facilitated by sonication and/or homogenisation.

Step (a) may be performed, for example, by using the methods described in WO 2004/011537 A1 (COOPER et al), which is hereby duly incorporated by reference.

In a particular embodiment, step (a) comprises:
  (i) providing an oil phase comprising lopinavir;
  (ii) providing an aqueous phase comprising the hydrophilic polymer and surfactant; and
  (iii) mixing the oil phase and aqueous phase to produce the oil in water emulsion.

Suitably, the oil phase is provided by dissolving lopinavir in a suitable organic solvent.

Suitably, the aqueous phase is provided by dissolving hydrophilic polymer and surfactant in an aqueous medium, preferably in water. Alternatively the aqueous phase may be provided by mixing two separately prepared aqueous solutions of the surfactant and hydrophilic polymer.

In a particular embodiment, further aqueous medium (e.g. water) or organic solvent is added before or during mixing step (iii).

The concentration of lopinavir in the oil in water emulsion is suitably as concentrated as possible to facilitate effective scale-up of the process. For example, the concentration of lopinavir in the oil phase is suitably 5 to 75 mg/ml, more suitably 10 to 70 mg/ml.

The concentration of the hydrophilic polymer in the aqueous/water phase is suitably 0.5-50 mg/mL, more suitably 10 to 30 mg/ml.

The concentration of the surfactant in the aqueous/water phase emulsion is suitably 0.5 to 50 mg/mL, more suitably 10 to 30 mg/ml.

The organic solvent forming the oil phase is (substantially) immiscible with water. Suitably the organic solvent is aprotic. Suitably the organic solvent has a boiling point less than 120° C., suitably less than 100° C., suitably less than 90° C.

In a particular embodiment, the organic solvent is a selected from the Class 2 or 3 solvents listed in the International Conference on Harmonization (ICH) guidelines relating to residual solvents.

In a particular embodiment, the organic solvent is selected from chloroform, dichloromethane, dichloroethane, tetrachloroethane, cyclohexane, hexane(s), isooctane, dodecane, decane, methylbutyl ketone (MBK), methylcyclohexane, tetrahydrofuran, toluene, xylene, butyl acetate, mineral oil, tert-butylmethyl ether, heptanes(s), isobutyl acetate, isopropyl acetate, methyl acetate, methylethyl ketone, ethyl acetate, ethyl ether, pentane, and propyl acetate, or any suitably combination thereof.

In a particular embodiment, the organic solvent is selected from chloroform, dichloromethane, methylethylketone (MEK), methylbutylketone (MBK), and ethyl acetate.

The volume ratio of aqueous phase to oil phase in mixing step (iii) is suitably between 20:1 and 1:4, more suitably between 10:1 and 1:1, most suitably between 6:1 and 2:1.

Mixing step (iii) suitably produces a substantially uniform oil in water emulsion. As previously indicated, mixing may be performed using methods well known in the art. Suitably, mixing step (iii) involves stirring, sonication, homogenisation, or a combination thereof. In a particular embodiment, mixing step (iii) involves sonication and/or homogenisation.

Step (b) may be performed using methods well known in the art. Suitably step (b) involves freeze drying, spray drying or spray granulation.

Step (b) may be performed using methods described in WO 2004/011537 A1 (COOPER et al), the entire contents of which are hereby incorporated by reference.

In a particular embodiment, step (b) involves freeze drying the oil in water emulsion. As such, step (b) may suitably comprise freezing the oil in water emulsion and then removing the solvents under vacuum.

Preferably, the freezing of the oil in water emulsion may be performed by externally cooling the oil in water emulsion. For example, a vessel containing the oil in water emulsion may be externally cooled, for example, by submerging the vessel in a cooling medium, such as liquid nitrogen. Alternatively the vessel containing the oil in water emulsion may be provided with an external "jacket" through which coolant is circulated to freeze the oil in water emulsion. Alternatively the vessel may comprise an internal element through which coolant is circulated in order to freeze the oil in water emulsion.

In a further alternative, the oil in water emulsion is frozen by being contacted directly with a cooling medium at a temperature effective for freezing the emulsion. In such cases, the cooling medium (e.g. liquid nitrogen) may be added to the oil in water emulsion, or the oil in water emulsion may be added to the cooling medium.

In a particular embodiment, the oil in water emulsion is added to the fluid medium (e.g. liquid nitrogen), suitably in a dropwise manner. This order of addition provides higher purities of final product. As such, frozen droplets of the oil in water emulsion may suitably form. Such frozen droplets may suitably be isolated (e.g. under vacuum to remove the fluid medium/liquid nitrogen). The solvent is then suitably removed from the frozen droplets under vacuum. The resulting solid composition is then isolated.

In an alternative aspect, the present invention provides a process for preparing a solid composition as defined herein, the process comprising:

preparing a single phase solution comprising lopinavir, a hydrophilic polymer as defined herein, and a surfactant as defined herein, in one or more solvents; and spray-drying the mixture to remove the one or more solvents to form the solid composition.

In this aspect of the invention, the single phase solution comprising the lopinavir, hydrophilic polymer, and surfactant are all dissolved in one solvent or two or more miscible solvents. Such processes are well described in WO 2008/006712, the entire contents of which are duly incorporated herein by reference. WO 2008/006712 also lists suitable solvents and combinations thereof for forming the single phase solution. In an embodiment, the single phase solution comprises two or more solvents (e.g. ethanol and water) which together solubilise lopinavir, hydrophilic polymer, and the surfactant. In another embodiment, the single phase comprises a single solvent, for example ethanol or water. Removing of the one or more solvents from the single phase fluid mixture involves spray drying—again WO 2008/006712 details suitable spray-drying conditions.

The present invention also provides a solid composition obtainable by, obtained by, or directly obtained by any of the processes described herein.

Aqueous Dispersion

The present invention provides an aqueous dispersion, comprising a plurality of nanoparticles dispersed in an aqueous medium, the nanoparticles comprising a core of lopinavir and a coating of at least one hydrophilic polymer and at least one surfactant;

wherein the hydrophilic polymer is selected from polyvinyl alcohol (PVA), a polyvinyl alcohol-polyethylene glycol graft copolymer, a block copolymer of polyoxyethylene and polyoxypropylene, polyethylene glycol, hydroxypropyl methyl cellulose (HPMC), and polyvinylpyrrolidone, or a combination thereof; and wherein the surfactant is selected from vitamin-E-polyethylene glycol-succinate (Vit-E-PEG-succinate), a polyoxyethylene sorbitan fatty acid ester, N-alkyldimethylbenzylammonium chloride, sodium deoxycholate, dioctyl sodium sulfosuccinate, polyethyleneglycol-12-hydroxystearate, polyvinyl alcohol (PVA), and a block copolymer of polyoxyethylene and polyoxypropylene, or a combination thereof.

The present invention also provides an aqueous dispersion, obtainable by, obtained by, or directly obtained by dispersing the solid composition as defined herein in an aqueous medium. Suitably, an aqueous dispersion is prepared immediately prior to use.

When the solid composition is dispersed in the aqueous medium, the hydrophilic polymer and/or surfactant is dissolved within the aqueous medium to release the nanoparticles of lopinavir in a dispersed form. The nanoparticles of lopinavir, which were formerly dispersed within a solid mixture of the hydrophilic polymer and surfactant, then become dispersed within the aqueous medium in a coated form, whereby the core of lopinavir is coated with the hydrophilic polymer and surfactant. Such a coating is thought to impart stability to the nanoparticles, thereby preventing premature coagulation and aggregation.

Suitably the relative amounts (including ratios) of lopinavir, hydrophilic polymer, and surfactant are the same as defined in relation to the solid composition. However, their respective wt % values in the aqueous dispersion as a whole must be adjusted to take account of the aqueous medium. In a particular embodiment, the aqueous medium comprises 20 to 99.5 wt % of the total aqueous dispersion. In a particular embodiment, the aqueous medium comprises 50 to 98 wt % of the total aqueous dispersion. In a particular embodiment, the aqueous medium comprises 70 to 95 wt % of the total aqueous dispersion. Suitably, the remaining proportion of the aqueous dispersion essentially consists of lopinavir, hydrophilic polymer, and surfactant, whose proportions within the aqueous dispersion as a whole are accordingly calculated (and scaled) by reference to the proportions recited in relation to the solid composition.

In a particular embodiment, the aqueous medium is water. In an alternative embodiment, the aqueous medium comprises water and one or more additional pharmaceutically acceptable diluents or excipients.

Aqueous dispersions of the present invention are advantageously stable for prolonged periods, both in terms of chemical stability and the stability of the particles themselves (i.e. with respect to aggregation, coagulation, etc.).

Aqueous dispersions of the present invention may be considered as pharmaceutical compositions of the present invention.

Aqueous dispersions of the present invention allow a measured aliquot to be taken therefrom for accurate dosing in a personalised medicine regime.

The particle size, polydispersity and zeta potential of the nanoparticles of lopinavir in the aqueous dispersion is as defined hereinbefore in relation to the solid composition. It will of course be appreciated that the particle size, polydispersity and zeta potential nanoparticles of lopinavir present in the solid composition are measured by dispersing the solid composition in an aqueous medium to thereby form an aqueous dispersion of the present invention.

In an embodiment, the aqueous dispersion comprises a single hydrophilic polymer and a single surfactant selected from those listed herein. In an alternative embodiment, the aqueous dispersion comprises two or more hydrophilic polymers and/or two or more surfactant selected from those listed herein.

Process for Preparing an Aqueous Dispersion

The aqueous dispersion may be formed by methods well known in the art. For example, lopinavir may be milled in the presence of an aqueous mixture of the hydrophilic polymer and surfactant.

In a particular aspect of the invention, however, there is provided a process for preparing an aqueous dispersion, comprising dispersing a solid lopinavir composition as defined herein in an aqueous medium.

In a particular embodiment, the aqueous medium is water. In an alternative embodiment, the aqueous medium comprises water and one or more additional excipients.

Dispersing the solid composition in the aqueous medium may comprise adding the solid composition to an aqueous medium and suitably agitating the resulting mixture (e.g. by shaking, homogenisation, sonication, stirring, etc.).

Pharmaceutical Compositions

The present invention provides a pharmaceutical composition comprising a solid composition or an aqueous dispersion as defined herein. The pharmaceutical compositions of the present invention may further comprise one or more additional pharmaceutically acceptable excipients.

The solid lopinavir compositions of the invention may be formulated into a form suitable for oral use (for example as tablets, lozenges, hard or soft capsules, or dispersible powders or granules) by techniques known in the art. As such, the solid compositions of the invention may be mixed with one or more additional pharmaceutical excipients during this process, such as antiadherants, binders, coatings, enterics, disintegrants, fillers, diluents, flavours, colours, lubricants, glidants, preservatives, sorbents, and sweeteners.

In a particular embodiment, the pharmaceutical composition is a tablet or capsule comprising the solid lopinavir composition.

The aqueous dispersion of the present invention may be administered as it is or further formulated with one or more additional excipients to provide a dispersion, elixir or syrup that is suitable for a oral use, or a dispersion that is suitable for parenteral administration (for example, a sterile aqueous dispersion for intravenous, subcutaneous, intramuscular, intraperitoneal or intramuscular dosing).

In a particular embodiment, the pharmaceutical composition is an aqueous dispersion as described herein. Such dispersed formulations can be used to accurately measure smaller dosages, such as those suitable for administration to children.

In a particular embodiment, the pharmaceutical composition is in a form suitable for parenteral delivery, whether via intravenous or intramuscular delivery.

It will be appreciated that different pharmaceutical compositions of the invention may be obtained by conventional procedures, using conventional pharmaceutical excipients, well known in the art.

The pharmaceutical compositions of the invention contain a therapeutically effective amount of lopinavir. A person skilled in the art will know how to determine and select an appropriate therapeutically effective amount of lopinavir to include in the pharmaceutical compositions of the invention.

Uses of the Nanoparticles Formulation and Pharmaceutical Composition

The present invention provides a solid composition or an aqueous dispersion as defined herein for use as a medicament.

In principle, the solid composition or aqueous dispersion defined herein can be used for the treatment of any virus that comprises a protease enzyme.

In a particular aspect, the present invention further provides a solid composition or an aqueous dispersion as defined herein for use in the treatment and/or prevention of retroviral infections (e.g. HIV).

The present invention further provides a use of a solid composition or an aqueous dispersion as defined herein in the manufacture of a medicament for use in the treatment and/or prevention of retroviral infections (e.g. HIV).

The present invention further provides a method of treating and/or preventing a retroviral infection (e.g. HIV), the method comprising administering a therapeutically effective amount of a solid composition, an aqueous dispersion, or a pharmaceutical composition as defined herein, to a patient suffering from or at risk of suffering from a retroviral infection.

The term "retrovirus" generally refers to an RNA virus capable of self-duplication in a host cell using the reverse transcriptase enzyme to transcribe its RNA genome into DNA. The DNA is then potentially incorporated into the host's genome so that the virus can then replicate thereafter as part of the host's DNA.

The retroviral infection to be treated or prevented is suitably selected from human immunodeficiency virus (HIV), Alpharetrovirus, Betaretrovirus, Gammaretrovirus, Deltaretrovirus, Epsilonretrovirus, Lentivirus, Spumavirus, Metavirus, Errantvirus, Pseudovirus, Hepadnavirus, and Caulimovirus.

In a particular embodiment of the present invention, the retroviral infection to be treated or prevented is the human immunodeficiency virus (HIV), most suitably the human immunodeficiency virus (HIV) type 1.

The solid compositions, aqueous dispersions, and pharmaceutical compositions of the present invention are also suitably used to reduce the risk of or prevent HIV infection developing in subjects exposed to a risk of developing HIV infection.

Lopinavir, the active agent in the solid compositions, aqueous dispersion, and pharmaceutical compositions of the present invention, is an anti-retroviral drug which acts as a protease inhibitor. As such, the solid composition, aqueous dispersion, and pharmaceutical compositions of the present invention are capable of inhibiting protease activity. Moreover, the nanoparticles and pharmaceutical compositions of the present invention are suitable for use in antiretroviral therapies and prophylactic treatments.

Thus in another aspect of the invention there is provided a method of inhibiting protease activity in a cell (in vivo or in vitro), the method comprising administering to said cell a solid composition, aqueous dispersion, or pharmaceutical composition as described herein.

In another aspect, the present invention provides a method of inhibiting protease activity in a human or animal subject in need of such inhibition, the method comprising administering to said subject an effective amount of a solid composition, aqueous dispersion, or pharmaceutical composition as defined herein.

In another aspect, the present invention provides a solid composition, aqueous dispersion, or pharmaceutical composition as defined herein for use in the treatment of a disease or condition associated with protease activity.

In another aspect, the present invention provides the use of a solid composition, aqueous dispersion, or pharmaceutical composition as defined herein in the manufacture of a medicament for use in the treatment of a disease or condition associated with protease activity.

Liponavir has also been shown to possess some activity against malaria. Thus, in yet another aspect, the solid composition or aqueous dispersion defined herein can be used for the treatment of malaria.

Routes of Administration

The solid compositions, aqueous dispersions, and pharmaceutical compositions of the invention may be administered to a subject by any convenient route of administration.

Routes of administration include, but are not limited to, oral (e.g. by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, infraarterlal, intracardiac, intrathecal, intraspinal, intracapsular, subcapsular, intraorbital, intraperitoneal, intratracheal, subcuticular, intraarticular, subarachnoid, and intrasternal; or by implant of a depot or reservoir, for example, subcutaneously or intramuscularly.

In a particular embodiment (e.g. in HIV treatments), the route of administration is either oral or by implant of a depot or reservoir formulation.

Combination Therapy

Although it is possible that the solid compositions, aqueous dispersions, and pharmaceutical compositions of the invention may be used as a sole medicament in the treatment and/or prevention of a retrovirus infection such as HIV, it is more typical that this agent will be used in combination with one or more additional anti-retroviral and/or anti-microbial agents.

Other antiretroviral agents suitable in combination treatments with the formulations and compositions of the present invention include Zidovudine, Zalcitabine, Didanosine, Stavudine, Lamivudine, Abacavir, Combivir (zidovudine+lamivudine), Trizivir (zidovudine+lamivudine+abacavir), Tenofovir, Emtricitabine, Truvada (Tenofovir+Emtricitabine), Epzicom/Kivexa (abacavir+lamivudine), Hydroxyurea, Nevirapine, Delavirdine, Etravirine, Rilpivirine, Atripla (lopinavir+emtricitabine+tenofovir), Indinavir, Ritonavir, Saquinavir, Nelfinavir, Amprenavir, Kaletra (lopinavir+ritonavir), Atazanavir, Fosamprenavir, Tipranavir, Darunavir, Enfuvirtide, Maraviroc, Raltegravir, Nevirapine, Efavirenz, Delavirdine, Etravirine, Rilprivrine, Artipla, or combinations thereof.

In a particular embodiment, the other suitable antiretroviral agents suitable for use in combination treatments with the formulations and compositions of the present invention include Tenofovir, Lamivudine, Abacavir, Emtricitabine, Zidovudine, Combivir (zidovudine+lamivudine), Truvada (Tenofovir+Emtricitabine), Epzicom/Kivexa (abacavir+lamivudine), and Ritonavir, or combinations thereof.

In a preferred embodiment, the other antiretroviral agents suitable for use in combination treatments with the formulations and compositions of the present invention include two of the following: Tenofovir, Lamivudine, Abacavir, Emtricitabine, Didanosine, Zidovudine.

In particular embodiments, the other antiretroviral agents suitable in combination with formulations and compositions of the present invention are themselves provided as combinations such as:

Emtricitabine+Tenofovir disoproxil fumarate
Lamivudine+Stavudine
Lamivudine+Tenofovir disoproxil fumarate
Lamivudine+Zidovudine
Lamivudine+Didanosine.

In a particular embodiment, the other suitable antiretroviral agent suitable for use in combination treatments with the formulations and compositions of the present invention is Ritonavir.

Accordingly, an aspect of the invention provides a combination suitable for use in the treatment or prevention of a retrovirus infection, such as HIV, comprising a solid composition, an aqueous dispersion, or a pharmaceutical composition as defined hereinbefore, and one or more other antiretroviral agents.

The present invention also provides a solid composition, an aqueous dispersion, or a pharmaceutical composition as defined hereinbefore for use in the treatment or prevention of a retrovirus infection, such as HIV, wherein the solid composition, aqueous dispersion, or pharmaceutical composition is administered in combination with one or more other antiretroviral agents.

In a further aspect, the present invention provides a pharmaceutical composition comprising a solid lopinavir composition as defined herein and one or more additional antiretroviral agents.

In a further aspect, the present invention provides a pharmaceutical composition comprising an aqueous dispersion as defined herein which further comprises one or more additional antiretroviral agents.

Herein, where the term "combination" is used it is to be understood that this refers to simultaneous, separate or sequential administration. In one aspect of the invention "combination" refers to simultaneous administration. In another aspect of the invention "combination" refers to separate administration. In a further aspect of the invention "combination" refers to sequential administration. Where the administration is sequential or separate, the delay in administering the second component should not be such as to lose the beneficial effect of the combination.

Such conjoint treatment may be achieved by way of the simultaneous, sequential or separate dosing of the individual components of the treatment. Such combination products employ the formulations or compositions of this invention within the dosage range described hereinbefore and the other pharmaceutically-active agent within its approved dosage range.

In a further aspect of the invention, there is provided a pharmaceutical composition comprising a solid composition or an aqueous dispersion as defined herein; and one or more other antiretroviral agents. In a particular embodiment, the pharmaceutical composition is a single dosage form.

Kit of Parts

The present invention provides a kit of parts comprising a solid composition as defined herein or pharmaceutical composition comprising the solid composition as defined herein, and a pharmaceutically acceptable aqueous diluent.

The solid composition or pharmaceutical composition comprising the solid composition as defined herein can be dispersed into the diluent to provide an aqueous dispersion as defined herein. Either the entire dispersion can then be administered, or a proportion of it can be measured and then administered (thereby providing a means of administering different dosages to individual patients).

EXAMPLES

The following examples describe the preparation of embodiments of liponavir formulations according to the present invention, along with various analytical data.

Materials

All materials were purchased and used without further purification from Sigma-Aldrich unless specified otherwise.

Example 1—Screening for Nanoformulations—10 Hydrophilic Polymers, 16 Surfactants Samples are prepared using a 10 mgml$^{-1}$ stock solution of lopinavir (A) in chloroform, a 22.5 mgml$^{-1}$ of polymer (P) and a 22.5 mgml$^{-1}$ stock solution of surfactant (S). Stock solutions are added in the following proportion; 100 μl (A); 267 μl (P) and 133 μl (S), therefore solid mass ratio is; 10% (A), 60% (P) and 30% (S) in an 1:4 oil to water (O/W) mix. The mixtures are then emulsified using a probe sonicator (UP400S manufactured by Hielscher (Germany)), fitted with an H3 titanium probe) operated at 20% amplitude for 7 seconds followed by immediate cryogenic freezing.

A matrix of 160 samples (comprised of 10 different polymers and 16 surfactants) was prepared. Once all 160 samples had been prepared, they were lyophilised (Virtis benchtop K) for 42 hours to leave a dry porous product, the samples were then sealed in individual vials until analysis.

The polymers and surfactants employed in this screen are detailed in Table 1A and Table 1B below:

TABLE 1A

List of hydrophilic polymers initially screened

| Polymer | MW | m/dm^3 (22.5 mg/ml) |
|---|---|---|
| PEG 1k | 1000 | 0.00225 |
| F68 | 8400 | 0.000267857 |
| F127 | 12600 | 0.000178571 |
| Kollicoat | 45000 | 0.00005 |
| PVA | 9500 | 0.000236842 |
| PVP k30 | 30000 | 0.000075 |
| HPC | 80000 | 0.000028125 |
| HPMC | 10000 | 0.000225 |
| Hydrolysed gelatin | 1982 | 0.001135217 |
| NaCMC | 90000 | 0.000025 |

TABLE 1B

List of 16 Surfactants initially screened

| Surfactant | MW | m/dm^3 (22.5 mg/ml) |
|---|---|---|
| Na alginate | 155000 | 1.45161E−05 |
| Na Myristate | 250.35 | 0.008987418 |
| Na Deoxycholate | 414.55 | 0.005427572 |
| Na Caprylate | 166.19 | 0.013538721 |
| Vit E-peg-succinate | 1000 | 0.00225 |
| Sisterna 11 | 650 | 0.003461538 |
| Sisterna 16 | 650 | 0.003461538 |
| SDS | 288.38 | 0.007802205 |
| AOT | 444.56 | 0.005061184 |
| Chremophor EL | 2500 | 0.0009 |
| Solutol HS | 344.53 | 0.006530636 |
| Tween 20 | 1227 | 0.001833741 |
| Tween 80 | 1300 | 0.001730769 |
| Brij 58 | 1123.52 | 0.002002635 |
| Hyamine | 448.08 | 0.005021425 |
| CTAB | 364.46 | 0.006173517 |

Screen Analysis

Immediately prior to analysis, samples were dispersed by addition of 1 ml of water. The particle size of the active, organic nanoparticulate dispersion is then measured by dynamic light scattering (DLS) using a Malvern Zetasizer Nano ZS. 3 measurements using automatic measurement optimisation, Malvern Zetasizer software version 6.20 was used for data analysis. The particles were considered hits if the below criteria were met.

Nanodispersion Quality Assessment Criteria

A particle is determined a hit if it complies with the following criteria: Complete dispersion of the sample with no large particles visible, a particle Z-average <1000 nm, a polydispersity index (PDI)<0.5, a standard deviation between three scans <10% from average Z-average and two of the three DLS scans pass the size quality report. The size quality report incorporates 12 tests on the reliability of the data recorded and is automatically applied to each measurement by the Malvern Zetasizer software. These tests ensure that the sample is within a size range appropriate for DLS, has a PDI below 1, is within the correct concentration range and that the cumulant and distribution fit are good (i.e. the errors on the data are less than 0.005).

Table 10 below lists the hits in terms of suitable hydrophilic polymers and surfactants.

TABLE 1C hits of suitable hydrophilic polymers and surfactants (74 hits in all)

| Hydrophilic Polymer | Surfactant |
|---|---|
| PEG 1K | Vit E-peg-succinate |
| PEG 1K | Chremophor EL |
| PEG 1K | Solutol HS |
| PEG 1K | Tween 80 |
| PEG 1K | Brij 58 |
| Pluronic F68 | Na Caprylate |
| Pluronic F68 | Vit E-peg-succinate |
| Pluronic F68 | AOT |
| Pluronic F68 | Chremophor EL |
| Pluronic F68 | Tween 20 |
| Pluronic F68 | Tween 80 |
| Pluronic F68 | Brij 58 |
| Pluronic F127 | Na alginate |
| Pluronic F127 | Na Deoxycholate |
| Pluronic F127 | Na Caprylate |
| Pluronic F127 | Sisterna 11 |
| Pluronic F127 | AOT |
| Pluronic F127 | Solutol HS |
| Pluronic F127 | Tween 20 |
| Pluronic F127 | Tween 80 |
| Pluronic F127 | Brij 58 |
| Pluronic F127 | Hyamine |
| Kollicoat | Na alginate |
| Kollicoat | Na Deoxycholate |
| Kollicoat | Na Caprylate |
| Kollicoat | Vit E-peg-succinate |
| Kollicoat | AOT |
| Kollicoat | Chremophor EL |
| Kollicoat | Solutol HS |
| Kollicoat | Tween 20 |
| Kollicoat | Tween 80 |
| Kollicoat | Brij 58 |
| Kollicoat | Hyamine |
| PVA | Na alginate |
| PVA | Na Deoxycholate |
| PVA | Na Caprylate |
| PVA | Vit E-peg-succinate |
| PVA | Sisterna 11 |
| PVA | Sisterna 16 |
| PVA | Chremophor EL |
| PVA | Solutol HS |
| PVA | Tween 20 |
| PVA | Tween 80 |
| PVA | Brij 58 |
| PVA | Hyamine |
| PVP 30K | Vit E-peg-succinate |
| PVP 30K | AOT |
| PVP 30K | Chremophor EL |
| PVP 30K | Solutol HS |
| PVP 30K | Tween 80 |
| PVP 30K | Hyamine |
| HPC | Na Caprylate |
| HPC | AOT |
| HPC | Tween 20 |
| HPC | Tween 80 |
| HPMC | Na Myristate |
| HPMC | Vit E-peg-succinate |
| HPMC | SDS |
| HPMC | AOT |
| HPMC | Chremophor EL |
| HPMC | Solutol HS |
| HPMC | Tween 20 |
| HPMC | Tween 80 |
| HPMC | Brij 58 |
| HPMC | Hyamine |
| Hydrolysed gelatine | Na Deoxycholate |
| Hydrolysed gelatine | AOT |
| Hydrolysed gelatine | Chremophor EL |
| Hydrolysed gelatine | Tween 80 |
| Hydrolysed gelatine | Brij 58 |
| Hydrolysed gelatin | Hyamine |
| NaCMC | Chremophor EL |
| NaCMC | Brij 58 |
| NaCMC | Hyamine |

Example 2—Nanoformulations Assessed in Biological Assays

'Hits' (i.e. those listed under Example 1 in Table 10) from the previous screen were remade in accordance with the procedures described in Example 1 in replicate (one sample to be characterised by DLS and zeta potential analysis, with an additional sample for each biological assay to be carried out).

Example 3—Radiolabelled Nanoformulations for Biological Assays $^{14}C$ radiolabelled efravirenz samples were prepared in order to carry out cell accumulation and transwell (i.e. transcellular permeability) pharmacology studies. The samples were prepared based on the hits from the previous two screens (i.e. Example 1 and 2), i.e. 74 hits of 60% (P):30% (S); and 77 hits of 75% (P):15% (S). The samples were prepared in triplicate; one cold batch for DLS analysis and two hot batches pharmacology study. Both the cold and hot samples were prepared following the same samples preparations mentioned previously. However, in order to prepare hot actives, 25 μC of 14C labelled LPV in ethanol was measured out. The solvent was allowed to evaporate away and the stock solution of cold LPV was added to the remaining solid, i.e. 286 mg in 28.6 ml of chloroform ((2×74)+(2×77) in 286×100 μl chloroform). The cold batches were then studied via DLS to determine both z-average and zeta potential.

Example 4—Preparing Higher Loading Nanoformulations (7 Hydrophilic Polymers, 7 Surfactants)

Samples were prepared containing a higher loading of lopinavir, using the hydrophilic polymers and surfactants listed below in Table 4A.

TABLE 4A

Hydrophilic polymers and surfactants employed

| Hydrophilic Polymer | Surfactant |
|---|---|
| PEG 1k | Na Deoxycholate |
| F68 | Vit E-peg-succinate |
| F127 | AOT |
| Kollicoat | Solutol HS |
| PVA | Tween 20 |
| PVP k30 | Tween 80 |
| HPMC | Hyamine |

The hydrophilic polymers and surfactants were selected based on the hits from the previous screens, focussing particularly on approved excipients appearing on the current FDA CDER list. The above 7 hydrophilic polymers and 7 hydrophilic surfactants were also selected based on their ability to provide successful formulations of lopinavir.

Samples are prepared using a 70 mgml$^{-1}$ stock solution of lopinavir (A) in chloroform, a 22.5 mgml$^{-1}$ of polymer (P) and a 22.5 mgml$^{-1}$ stock solution of surfactant (S). Stock solutions are added in the following proportion; 100 μl (A); 90 μl (P) 45 μl (S) and 265 μl of water, therefore solid mass ratio is; 70% (A), 20% (P) and 10% (S) in an 1:4 oil to water (O/W) mix. The mixtures are the emulsified using a Covaris S2× for 30 seconds with a duty cycle of 20, an intensity of 10 and 500 cycles/burst in frequency sweeping mode. After which, the samples were immediately cryogenically frozen. A matrix of 49 samples (comprised of 7 different polymers and 7 surfactants) was prepared. Once all 49 samples had been prepared, they were lyophilised (Virtis benchtop K) for 42 hours to leave a dry porous product, the samples were then sealed in individual vials until analysis.

High Loading (70% Active) Screen

Immediately prior to analysis samples were dispersed by addition of 3.5 ml of water. All analysis was carried out in the same way as described earlier in Example 1.

FIG. 1 shows a 3-D bar chart representing the clear hits in grey, near misses in white with dots, more distant misses in transparent, and non-hits without bars. The z-average particle size for each of the hits, near misses, and more distant misses is given on the vertical axis.

Example 5—High Loading (70% Active) Formulation Variation

The formulation space around 'hits' (i.e. grey bars) from the high loading screen of Example 4 was further investigated. Here, the surfactant to polymer ratio was varied at four levels shown in table 5A below.

TABLE 5A

Table showing variation in polymer/surfactant ratio

| Polymer (%) | Surfactant (%) | Polymer solution volume (μl) | Surfactant solution volume (μl) |
|---|---|---|---|
| 25 | 5 | 112.5 | 22.5 |
| 20 | 10 | 90 | 45 |
| 15 | 15 | 67.5 | 67.5 |
| 10 | 20 | 45 | 90 |

Samples are prepared using a 70 mgml$^{-1}$ stock solution of lopinavir (A) in chloroform, a 22.5 mgml$^{-1}$ of polymer (P) and a 22.5 mgml$^{-1}$ stock solution of surfactant (S). Stock solutions are added in the following proportion; 100 μl (A), 265 μl of water, with the volumes of polymer and surfactant solutions shown in the table above. All other preparation was the same as described in Example 4. The samples were then screened in the same manner as Example 4, and again hits are given in grey in FIG. 2.

Figure 2:
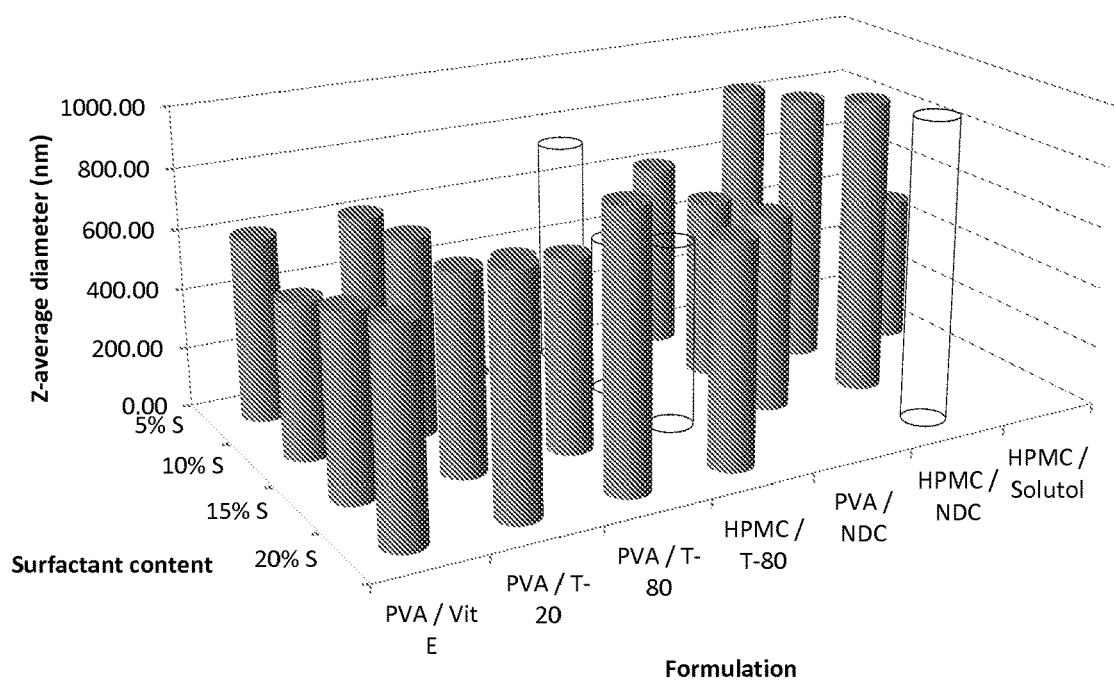
FIG. 2 shows a screen of the 7 hits from Example 4 herein using variable proportions of polymer/surfactant as described in Example 5 (clear "hits" (i.e. compositions satisfying the nanodispersion assessment criteria—set out in Example 1) are shown as grey bars, near misses (i.e. nanoparticles dispersed well but failed on the nanodispersion selection criteria) are shown as transparent bars, and non-hits are shown without bars).

FIG. 2 shows a screen of the 7 hits from Example 4 using variable proportions of polymer/surfactant Table 5B below provides further details of screen, a hit for each of the other combinations at a 5% surfactant loading (since lower surfactant quantities are desirable from a toxicity point of view).

TABLE 5B

Details of 7 hits from the Example 5 screening experiments

| | % Surfactant | Z-Av Original | Z-Av Repeat | Z-Av AV | SD % from AV | Re-Made |
|---|---|---|---|---|---|---|
| PVA/Vit E | 5% | 608.7 | 570.4 | 589.6 | 4.6 | 10% S |
| PVA/T-20 | 5% | 621.6 | 579.0 | 600.3 | 5.0 | 10% S |
| PVA/T-80 | 10% | 523.3 | 602.6 | 562.9 | 10.0 | 15% S |
| HPMC/T-80 | 20% | 739.9 | N | — | — | — |
| PVA/NDC | 5% | 617.5 | 672.5 | 645.0 | 6.0 | 10% S |
| HPMC/NDC | 10% | 891.6 | 1135.0 | 1013.3 | 17.0 | — |
| HPMC/Solutol HS | 10% | 485.1 | N | — | — | — |

[N = sample did not disperse, so size data not collected]

As can be seen from Table 5B, two of the repeat samples, namely HPMC/T-80, HPMC/NDC and HPMC/Solutol HS, did not quite meet the above-described screening criteria, and therefore only 4 of the successful repeats were used for further experimentation.

Figure 3:
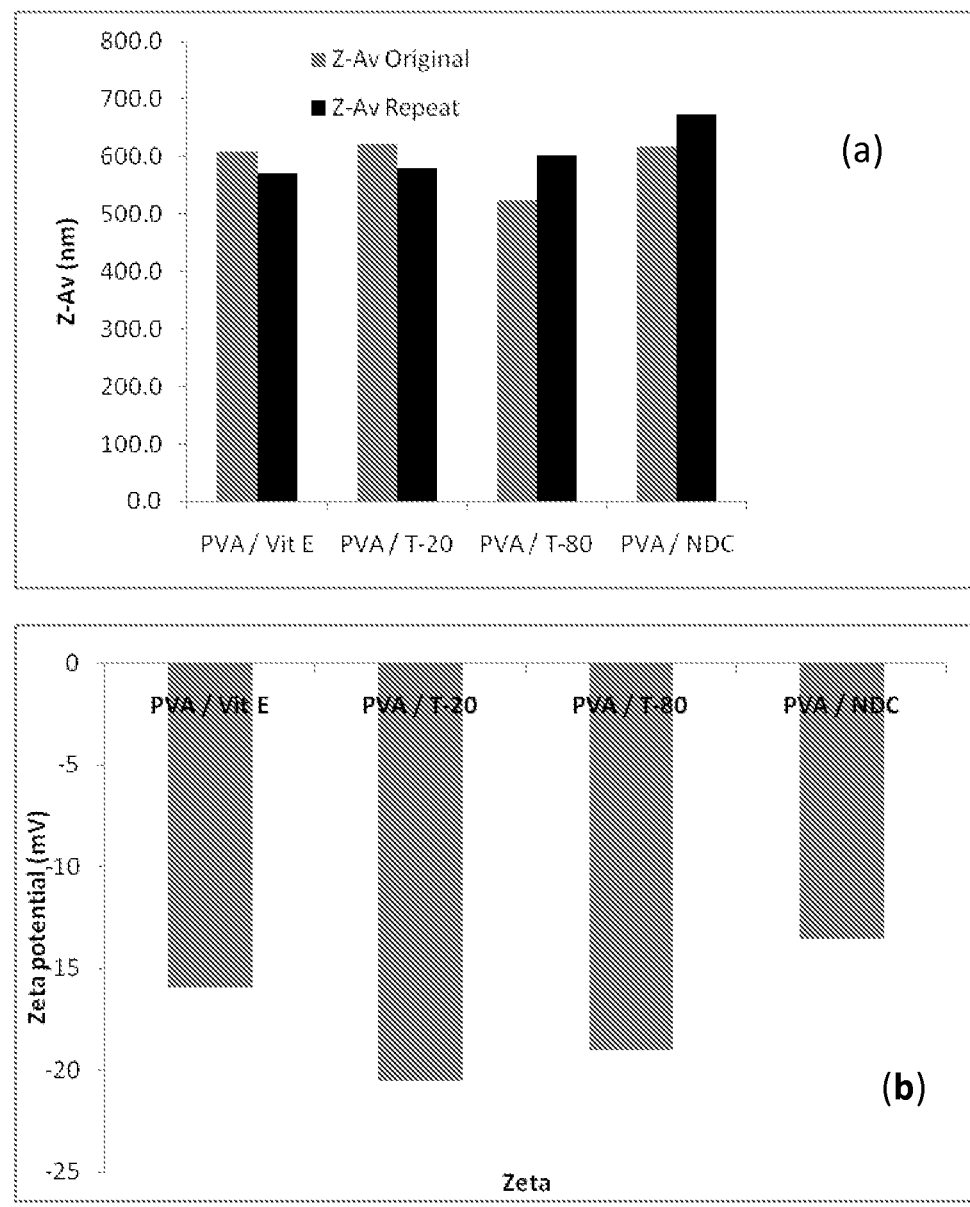
FIG. 3 shows (a) the z-average particle size (nm) for the original and repeat samples of each of the 4 successful repeat samples; and (b) the average zeta potential (mV) for each of the 4 successful repeat samples (see Example 5).

FIG. 3 shows (a) the z-average particle size (nm) for the original and repeat samples of each of the 4 successful repeat samples; and (b) the average zeta potential (mV) for each of the 4 successful repeat samples.

Table 5C shows analytical data for the 4 successful repeat samples, specifically the low % surfactant present (5% in all cases), z-average particle size of the original sample, z-average particle size of the repeat sample, average z-average particle size of both original and repeat, % standard deviation (SD) from the average, % surfactant in a further remade sample containing a high % of surfactant (10% in all cases), and the z-average particle size of the further high 10 surfactant sample.

TABLE 5C analytical data for the 4 successful repeat samples

| | Low % Surfactant | Z-Av Original | Z-Av Repeat | Z-Av AV | SD % from AV | High % Surfactant | Z Av |
|---|---|---|---|---|---|---|---|
| PVA/Vit E | 5% | 608.7 | 570.4 | 589.6 | 4.6 | 10% S | 585.1333 |
| PVA/T-20 | 5% | 621.6 | 579.0 | 600.3 | 5.0 | 10% S | 967.6 |
| PVA/T-80 | 10% | 523.3 | 602.6 | 562.9 | 10.0 | 15% S | 591 |
| PVA/NDC | 5% | 617.5 | 672.5 | 645.0 | 6.0 | 10% S | 667.5667 |

Figure 4:
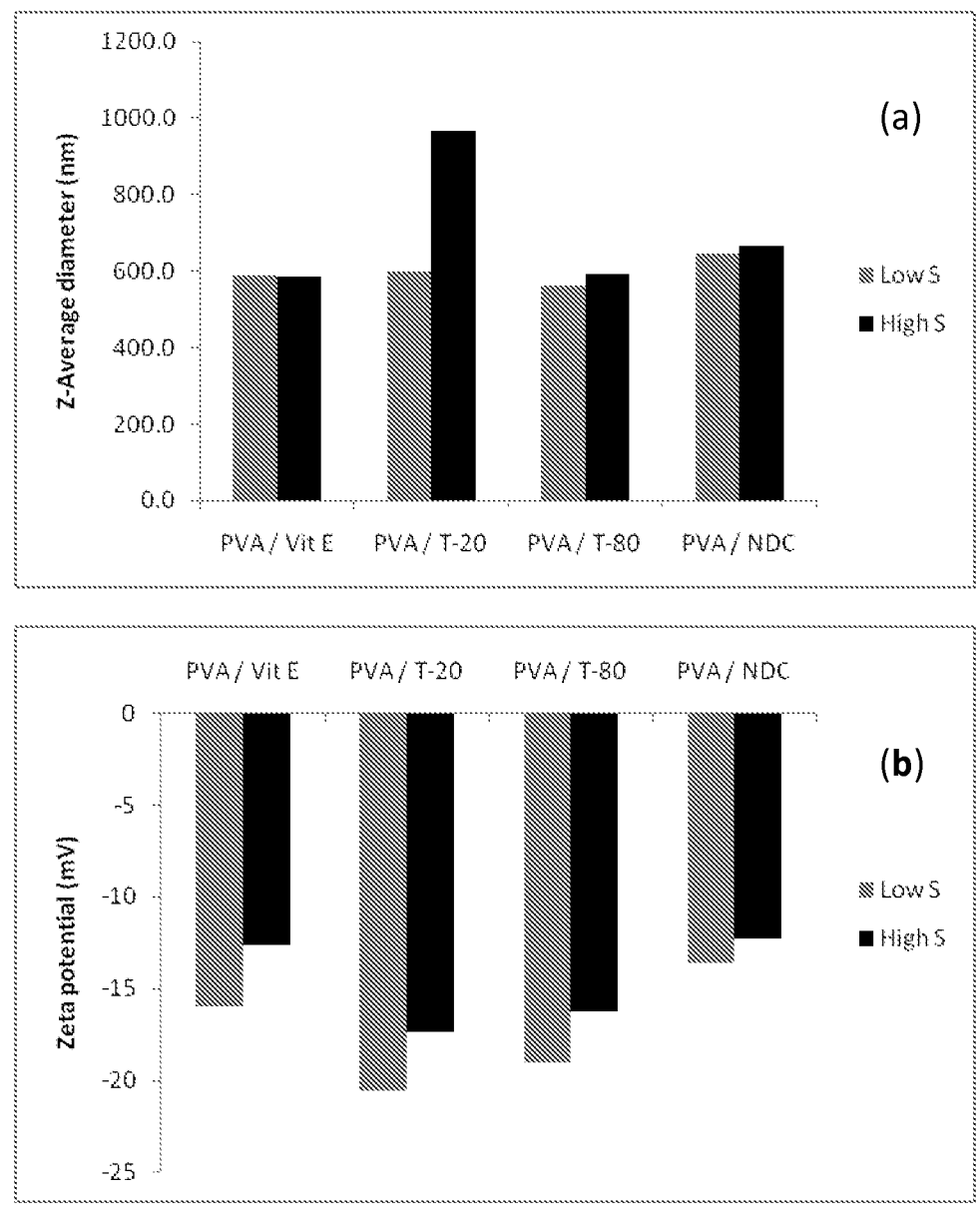
FIG. 4 shows (a) the z-average particle size (nm) for low surfactant (5%) and high surfactant (10%) samples detailed in Table 5C; and (b) the average zeta potential (mV) for low surfactant (5%) and high surfactant (10%) samples detailed in Table 5C (see Example 5).

FIG. 4 shows (a) the z-average particle size (nm) for low surfactant (5%) and high surfactant (10%) samples detailed in Table 5C; and (b) the average zeta potential (mV) for low surfactant (5%) and high surfactant (10%) samples detailed in Table 5C.

Example 6—High Loading Radiolabelled Nanoformulations for Biological Assays

From the above data in Example 5, 3 particular polymer/surfactant combinations were selected for further study. The three samples were selected on the basis that they showed good sample-to-sample reproducibility (i.e. a standard deviation below 10%). Further radiolabelled samples were prepared for the combinations of particular interest, namely PVA/Vit-E, PVA/T-80, and PVA/NDC.

Radiolabelled lopinavir samples were prepared in accordance with Example 3, however, the chloroform solution containing the lopinavir was also dosed with the radiolabelled active to give a tracer concentration of radioactivity for efravirenz samples. The samples were then used for all cellular accumulation and transcellular permeability studies.

Table 6A shows the z-average particle size (nm) and zeta potential (mV) analytical data in relation to original non-radiolabelled samples containing low (5%) and high (10%) surfactant concentrations, and also radiolabelled samples containing low (5%) and high (10%) surfactant concentrations.

TABLE 6A analytical data for non-radiolabelled (original) and radiolabelled samples

| | Original Samples | | | | Radiolabelled Samples | | | |
|---|---|---|---|---|---|---|---|---|
| | 5% Surfactant | | 10% Surfactant | | 5% Surfactant | | 10% Surfactant | |
| LPV | Z-Av | Zeta | Z-Av | Zeta | Z-Av | Zeta | Z-Av | Zeta |
| PVA/Vit-E | 589.6 | −16.0 | 585.1333 | −12.6 | 597.7667 | −11.6 | 548.0667 | −11 |
| PVA/T-20 | 600.3 | −20.5 | 967.6 | −17.3 | 599.4667 | −19.3 | 999.6667 | −21.8 |
| PVA/NDC | 645.0 | −13.6 | 667.5667 | −12.3 | 682.0667 | −14.8 | 733.8333 | −13.5 |

Nanodispersions of the cold (i.e. non-radiolabelled) samples were then analysed over time with respect to their z-average particle size, particle size polydispersity (i.e. diversity of particle sizes), and zeta potential.

Figure 5A:
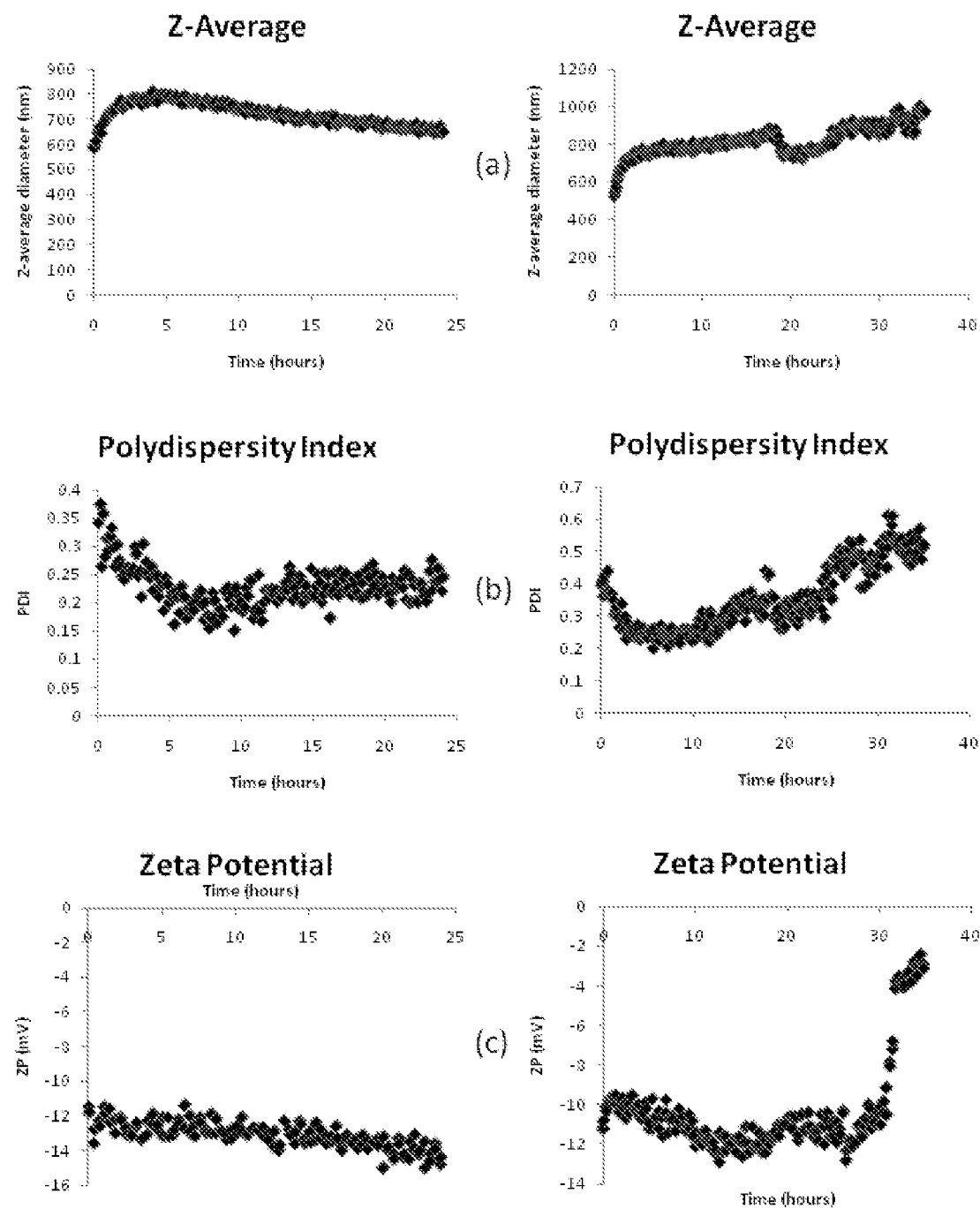
FIGS. 5A-5C demonstrate the stability of nanodispersions of lopinavir of the present invention over prolonged time periods (see Example 6).

FIG. 5A shows time course measurements made upon nanodispersions of the cold PVA/Vit-E samples (for both 5% and 10% surfactant samples) with respect to their (a) z-average particle size (nm); (b) particle size polydispersity; and (c) average zeta potential (mV), each for PVA/Vit-E samples comprising both 5% (left hand side) and 10% (right hand size) surfactant content.

Figure 5B:
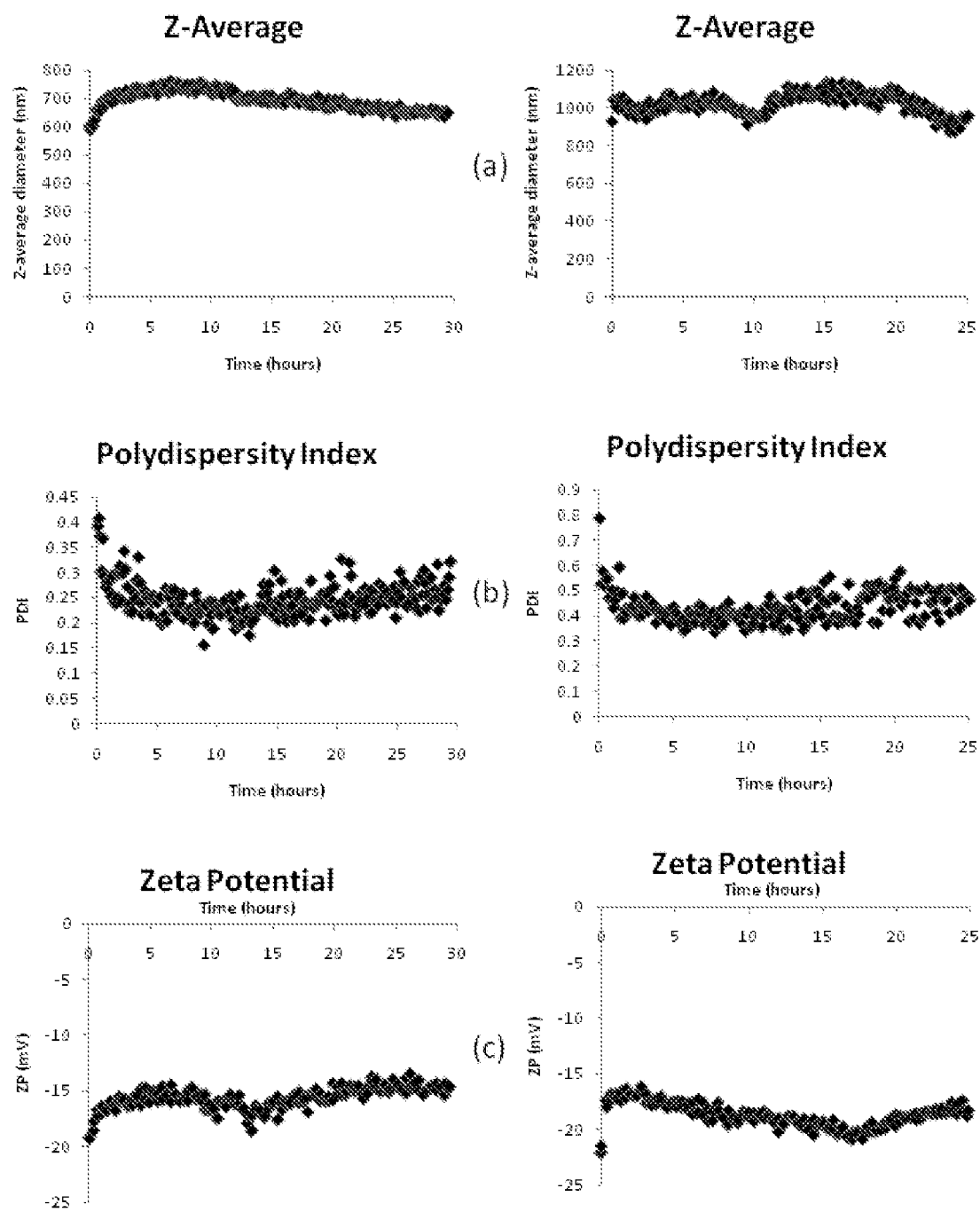

FIG. 5B shows time course measurements made upon nanodispersions of the cold PVA/T-20 samples (for both 5% and 10% surfactant samples) with respect to their (a) z-average particle size (nm); (b) particle size polydispersity; and (c) average zeta potential (mV), each for PVA/T-20 samples comprising both 5% (left hand side) and 10% (right hand size) surfactant content.

Figure 5C:
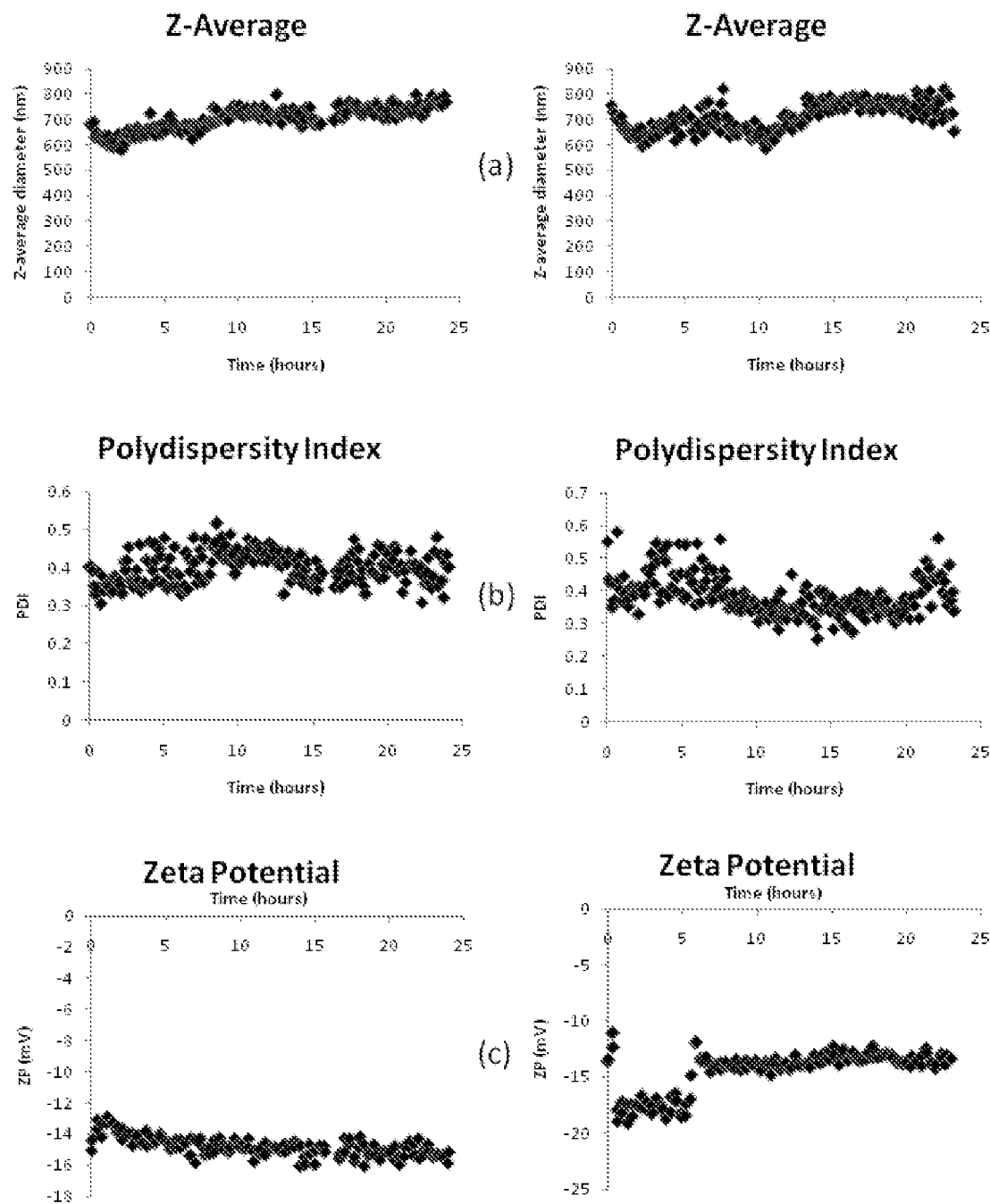

FIG. 5C shows time course measurements made upon nanodispersions of the cold PVA/NDC samples (for both 5% and 10% surfactant samples) with respect to their (a) z-average particle size (nm); (b) particle size polydispersity; and (c) average zeta potential (mV), each for PVA/NDC samples comprising both 5% (left hand side) and 10% (right hand size) surfactant content.

FIGS. 5A-5C demonstrate the stability of nanodispersions of lopinavir of the present invention over prolonged time periods.

Example 7—Cytotoxicity of Lopinavir Nanodispersions in Hepatic, Intestinal, Monocyte, Macrophage and Lymphocyte Cell Lines Routine Cell Culture/Cell Maintenance HepG2 (hepatic) and Caco-2 (intestinal) cells were purchased from American Type Tissue Culture (ATCC; USA) and maintained in Dulbecco's modified eagle's medium (DMEM; Sigma; Dorest, Uk) supplemented with 10% fetal bovine serum (FBS; Bio-Whittaker, Berkshire, Uk) for HepG2 and 15% FBS for Caco-2. CEM (lymphocyte) and THP-1 (monocyte) cells were purchased from European Collection of Cell Culture (ECACC; Porton Down, Uk) and grown in RPMI-1640 (Sigma; Dorest, Uk) supplemented with 10% FBS. All cell lines were incubated at 37° C. and 5% $CO_2$ and for adherent cells (HepG2 and Caco-2) were routinely sub-cultured every 4 days when 95% confluent. Suspension cells (CEM and THP-1) were routinely sub-cultured when a density of $1 \times 10^6$ cells/ml was achieved. Cell count and viability was determined by Trypan Blue exclusion assay.

Monocyte Derived Macrophages (MDM)

THP-1 cells were activated into macrophage like cells (A-THP-1) by the addition of Phorbol 12-myristate 13 acetate (PMA: Sigma; Dorest, Uk) to final concentration of 10 nM in THP-1 culture medium (RPMI-1640 supplemented with 10% FBS). Cells were then incubated at 37° C. and 5% $CO_2$ for 7 days prior to use to allow differentiation from monocyte to macrophage like cells.

HepG2, Caco-2, THP-1, CEM and A-THP-1 cells were separately seeded at a density of $2.5 \times 10^4 / 100$ μl in their appropriate media into each well of a 96 well plate (Nunclon™, Denmark) and incubated for 24 hours at 37° C. and 5% $CO_2$. Media was then aspirated and replaced with media containing 0.1, 1, 10, 100, 500 or 1000 μM, calculated from molarity of lopinavir (145 samples), of each lopinavir dispersion and incubated for a further 24 hours. The same procedure was followed for each individual excipient (23 samples) with concentrations range of 1 μM to 1M. The lopinavir dispersions in question are presented in Table 7 below.

TABLE 7

Six Nanodispersed Lopinavir Formulations

| Designation | Formulation |
|---|---|
| Nanodispersion 1 | 25% PVA/5% Vit-E-PEG-succinate |
| Nanodispersion 2 | 25% PVA/5% Tween 80 |
| Nanodispersion 3 | 25% PVA/5% sodium deoxycholate |
| Nanodispersion 4 | 20% PVA/10% Vit-E-PEG-succinate |
| Nanodispersion 5 | 20% PVA/10% Tween 80 |
| Nanodispersion 6 | 20% PVA/10% sodium deoxycholate |

ATP Cell Viability Assay (Promega: CellTiter-Glo® Luminescent)

Prior to starting viability assays, all reagents were made fresh and in accordance to manufacturer's instructions and allowed to equilibrate to room temperature immediately before use. After 24 hours incubation, 96 well plates were removed from the incubator and the plate and its contents allowed too equilibrate to room temperature for approximately 30 minutes. After 30 minutes, 80 μl of media was aspirated from each individual well and 20 μl CellTiter-Glo® Reagent (Promega, UK) was added to the remaining media and cells. The contents were then mixed for 2 minutes on an orbital shaker to induce cell lysis. The plate was then further incubated at room temperature for 10 minutes to stabilise luminescent signal. Luminescence was then measured using a Tecan Genios plate reader (Tecan; Austria).

Figure 6:
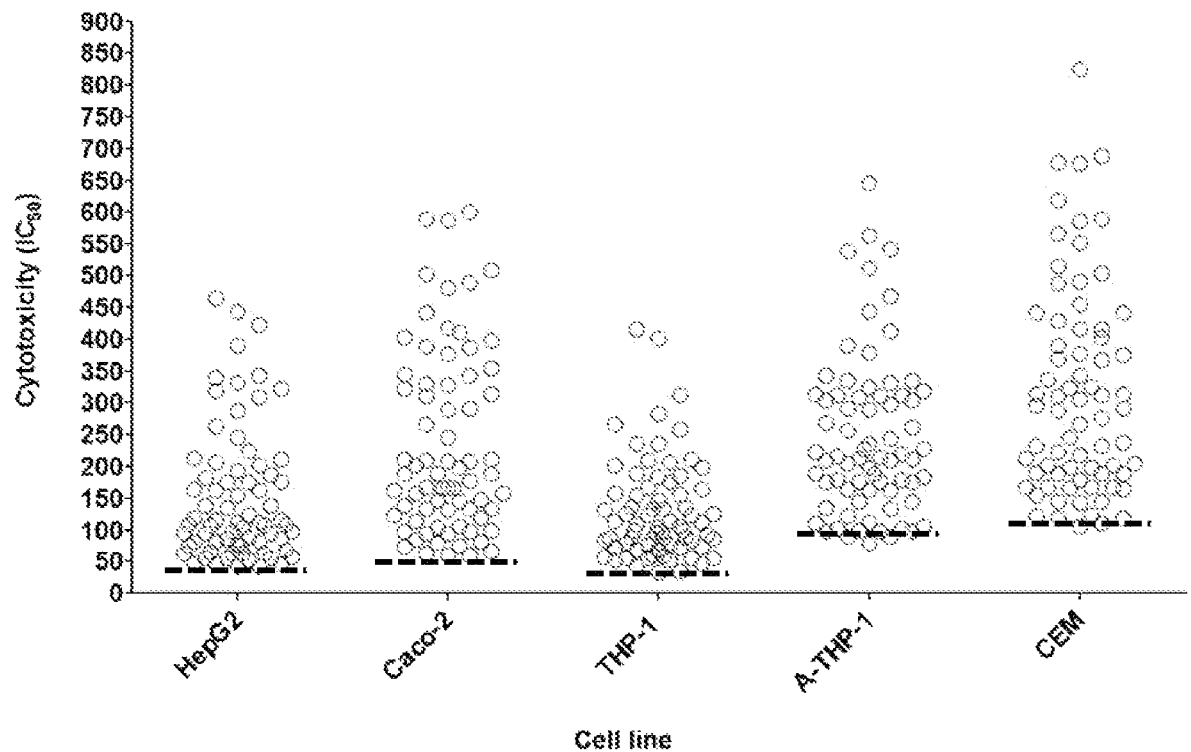
FIG. 6 shows the cytotoxicity of 10% lopinavir loaded nanodispersions across various cell lines. Data for aqueous lopinavir are given as dotted horizontal lines. Data are given as $IC_{50}$ in μM.

FIG. 6 provides data in relation to the cytotoxicity of the various 10% drug loaded lopinavir formulations in terms of $IC_{50}$ (μM). Table 8 provides data in relation to the cytotoxicity of the various 70% drug loaded lopinavir formulations in terms of $IC_{50}$ (μM).

TABLE 8

Cytotoxicity of 70% lopinavir loaded nanodispersions and aqueous lopinavir across various cell lines. Data are given as $IC_{50}$ in μM.

| Designation | Cell line | | | | |
|---|---|---|---|---|---|
| | HepG2 | Caco-2 | THP-1 | A-THP-1 | CEM |
| Nanodispersion 1 | 124.7 | 209.1 | 104.4 | 219.0 | 458.1 |
| Nanodispersion 2 | 185.3 | 252.6 | 77.2 | 173.5 | 239.9 |
| Nanodispersion 3 | 114.1 | 168.4 | 114.3 | 207.0 | 154.2 |
| Nanodispersion 4 | 90.7 | 186.2 | 81.9 | 189.1 | 457.4 |
| Nanodispersion 5 | 142.6 | 205.5 | 45.1 | 123.0 | 197.6 |
| Nanodispersion 6 | 75.3 | 145.5 | 86.7 | 158.4 | 128.4 |
| Aqueous solution | 35.8 | 52.5 | 28.3 | 84.3 | 100.4 |

In summary, the large majority of the 10% loaded nanodispersions were less cytotoxic than equivalent concentrations of aqueous lopinavir. For 70% loaded lopinavir nanodispersions, all were less cytotoxic than aqueous lopinavir in the studied cell systems.

Example 8—Inhibition of Recombinant HIV-1 Protease by Nanodispersed and Aqueous Lopinavir HIV-1 protease inhibition screening was conducted as per manufacturers' instructions (Roche Diagnostics GmbH; Germany). Briefly, for each of the individual nano dispersed lopinavir formulation, 20 μl of 1 nM stock was added to each well of row B of a 96 well plate ((Nunclon™, Denmark). Doubling dilutions were then preformed using deionised $H_2O$ to give a range of concentrations from 1 nM to 0.0078 nM for each sample. 20 μl of 0.2 ng/μl HIV-1-protease diluted in lysis buffer was then added to each well. 20 μl of reaction mixture (consisting of; 46 mM Tris-HCl, 266 mM potassium chloride, 27.5 mM magnesium chloride, 9.2 mM DTT, 10 μM dUTP/dTTP, template/primer hybrid, 750 $mA_{260nm}$/ml) was added to each well containing lopinavir sample and the plate incubated for 60 minutes at 37° C. The entire sample (60 μl) was then transferred into microplate modules and incubated for a further 60 minutes at 37° C. The samples were then aspirated and washed ×5 with 250 μl of wash buffer. After the final aspiration, 200 μl of reconstituted anti-digoxigenin-peroxidase (Anti-DIG-POD) polyclonal antibody (200 mU/ml final concentration) was added to all wells and the plate returned to the incubator for a further 60 minutes at 37° C. The samples were aspirated and washed ×5 with wash buffer. Finally, after the final wash buffer was aspirated, 200 μl of ABTS substrate was added to each well and the plate incubated at room temperature for 15 minutes. Absorbance was then measured at 405 nm using FLUOstar Omega microplate reader (BMG Labtech, Uk).

Figure 7:
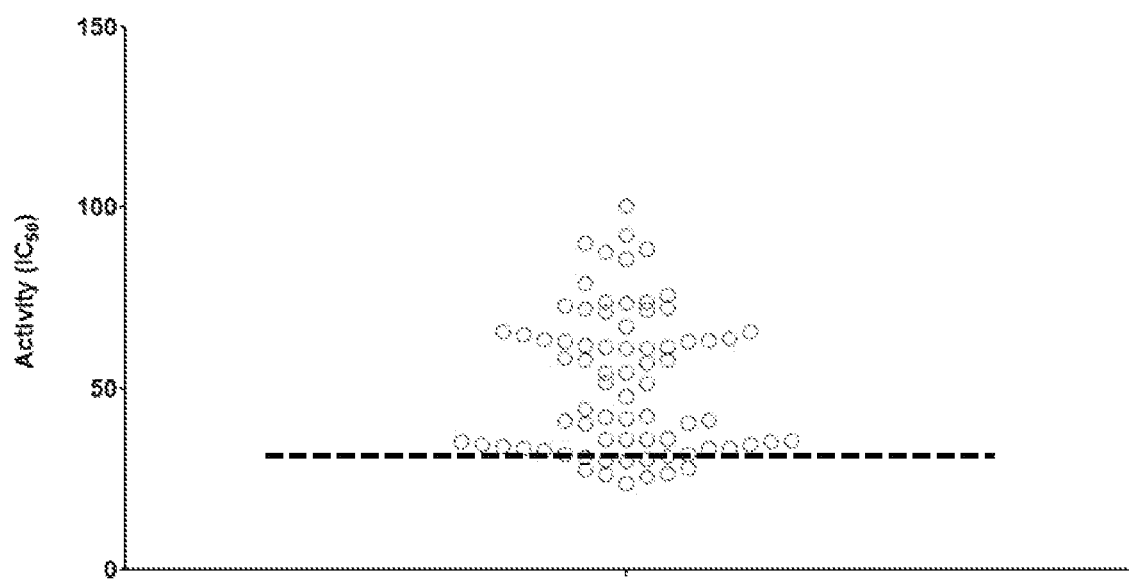
FIG. 7 shows the activity of 10% loaded lopinavir nanodispersions against recombinant HIV protease. Data for aqueous lopinavir are given as the dotted horizontal line. Data are given as $IC_{50}$ in nM.

The above procedure allowed for determination of the activity of the 10% drug loaded (see FIG. 7) and 70% drug loaded (see Table 9) lopinavir nanodispersions against the target protein, protease.

TABLE 9

Activity of 70% loaded lopinavir nanodispersions against recombinant HIV protease. Data are given as $IC_{50}$ in nM.

| Designation | $IC_{50}$ (nM) |
|---|---|
| Nanodispersion 1 | 28 |
| Nanodispersion 2 | 34 |
| Nanodispersion 3 | 60 |
| Nanodispersion 4 | 20 |
| Nanodispersion 5 | 29 |
| Nanodispersion 6 | 47 |
| Aqueous solution | 32 |

In summary, most of the 10% loaded nanodispersions exhibited equivalent activity to aqueous lopinavir for inhibition of recombinant HIV protease. For 70% loaded lopinavir nanodispersions, all were able to inhibit recombinant protease within the nM range. 3 of the 6 70% loaded nanodispersions exhibited equivalent or better activity against recombinant HIV protease. Data should be interpreted in light of this being a cell-free assay.

Example 9—Inhibition of Cultured HIV-IIIB by Nanodispersed and Aqueous Lopinavir in MT4 Cells MT4/HIVIII$_B$ Routine Cell Culture/Propagation HIVIII$_B$ and the human T-cell line, MT4, were supplied by the National Institute for Biological Standards and Control (NIBSC), the Centre for AIDS Reagents (CFAR: Hertfordshire, Uk). MT4 cells were grown and routinely maintained in RPMI-1640 (Sigma; Dorest, Uk) supplemented with 10% fetal bovine serum (FBS; Bio-Whittaker, Berkshire, Uk) at 37° C. and 5% $CO_2$ and sub-cultured every 3 days. Cell counts and viability was determined by Trypan Blue exclusion using a disposable plastic haemocytometer (Labtech International Ltd, UK). HIVIII$_B$ was propagated by passage through MT4 cells in RPMI-1640 and 10% FBS for 12 days and a subsequent multiplicity of infection (MOI) was determined by MTT assay.

Treatment of HIVIII$_B$ with Nanodispersed LOPINAVIR

MT4 cells were dispensed into 50 ml falcon tubes and centrifuged at 2000 rpm and 4° C. for 5 minutes. The supernantant was aspirated and the resulting pellet resuspended to a cell density of $1\times10^5$/ml in RPMI 1640 supplemented with 10% FBS and 1 ml of viral isolate (M.O.I 0.001). After further centrifugation for 5 minutes at 2000 rpm, the MT4/HIVIII$_B$ pellet was incubated at 37° C. and 5% $CO_2$ for 2 hours. Following incubation, the MT4/HIVI-II$_B$ suspension was centrifuged again at 2000 rpm and 4° C. for 5 minutes, supernatant aspirated and pellet resuspend RPMI 1640 supplemented with 10% FBS to a cell density of $1\times10^5$/ml.

100 μl of MT4/HIVIII$_B$ suspension was then added to each well of a flat bottomed 96 well plate (Nunclon™, Denmark) containing each of the individual nano dispersed Lopinavir (LOPINAVIR) formulations to give a range of final concentrations from 1 nM to 0.0078 nM. The plate was then incubated for 5 days at 37° C. and 5% $CO_2$.

Tetrazolium-Based Colorimetric (MTT) Assay Using MT4 Cells for the Detection of Anti-HIV Compounds Following incubation for 5 days of MT4/HIVIII$_B$ with nano formulated LOPINAVIR at 37° C. and 5% $CO_2$. 20 μl of 5 mg Thiazolyl Blue Tetrazolium (Sigma, Uk) per ml of Hanks balanced salt solution (HBSS: Sigma, Uk) was added to each well and then further incubated for 2 hours at 37° C. and 5% $CO_2$. 100 μl of lysis buffer containing 50% v/v dimethylformahyde (Sigma, Uk) and 20% v/v sodium dodecyl sulphate (Sigma, Uk) and incubate again for 24 hours. Absorbance was read at 570 nm on a plate reader (Tecan Magellan, Austria).

Figure 8:
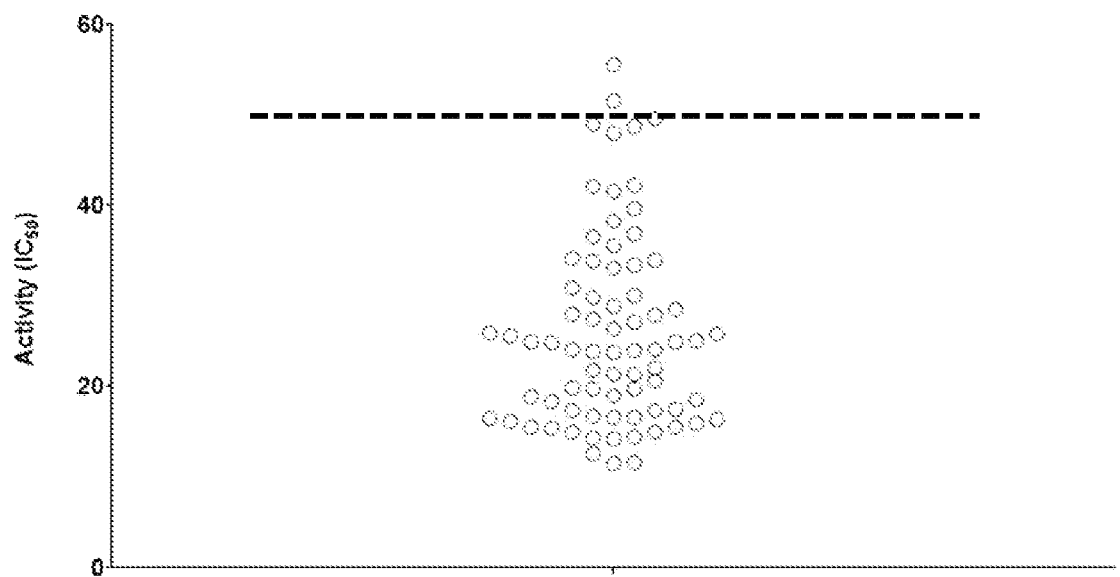
FIG. 8 shows the activity of 10% loaded lopinavir nanodispersions against $HIVIII_B$. Data for aqueous lopinavir are given as the dotted horizontal line. Data are given as $IC_{50}$ in nM.

The above procedures allowed for determination of the activity of the 10% drug loaded (FIG. 8) and 70% drug loaded (table 10 lopinavir nanodispersions against cultured HIV virus.

TABLE 10

Activity of 70% loaded lopinavir nanodispersions against recombinant HIV protease. Data are given as

| Designation | $IC_{50}$ (nM) |
|---|---|
| Nanodispersion 1 | 16 |
| Nanodispersion 2 | 27 |
| Nanodispersion 3 | 46 |
| Nanodispersion 4 | 12 |
| Nanodispersion 5 | 22 |
| Nanodispersion 6 | 29 |
| Aqueous solution | 56 |

In summary, most of the 10% loaded nanodispersions exhibited equivalent activity higher than that of aqueous lopinavir for inhibition of $HIVIII_B$. For 70% loaded lopinavir nanodispersions, all were able to inhibit recombinant protease within the nM range and all exhibited equivalent or better activity against $HIVIII_B$. Data should be interpreted in light of this being a cell-based assay (see example 13 for impact of nanoformulation on cellular accumulation).

Example 10—Cellular Accumulation of Nano Dispersed Lopinavir Compared to their Parental, Aqueous Compounds Cellular Accumulation of Nano Dispersed LOPINAVIR Compared to their Parental, Aqueous Compounds in Adherent Cell Lines; Caco-2, HepG2 and ATHP-1.

Cellular accumulation of nano dispersed LOPINAVIR was quantified in adherent cell lines, Caco-2 and HepG2 and ATHP-1's as follows. Caco-2/HepG2 were propagated to a cell density of ~5×10$^6$ cells per well on a 6 well plate (37° C. and 5% $CO_2$). The cells were washed ×2 with pre-warmed HBSS (37° C.). The cells were incubated for 1 h in the presence of 1 ml of HBSS containing 10 µM LOPINAVIR containing 0.1 µCi of $H^3/C^{14}/H^3$ labelled drug respectively. After 1 hr, an extracellular sample was taken from supernatant (100 µl and added into a 5 ml scintillation vial (Meridian Biotechnologies Ltd; Uk). The supernatant containing drug was aspirated from the well and cells washed ×2 in ice cold HBSS. The ice cold HBSS was aspirated and the addition of 500 µl of tap water to lyse the cells. The cellular debris plates (6 well) were stored overnight at −20° C. to aid lysis. The 500 µl of tap water was then used to pipette away cell debris from the well base and added to a 5 ml scintillation vial (Meridian Biotechnologies Ltd; Uk). To each 5 ml vial, 4 ml of Ultima Gold scintillation fluid was added and scintillation level quantified using a Perkin Elmeer 3100TS scintillation counter. Each nano-dispersion was tested in duplicate and scintillation measurements taken in triplicate.

This culture method is altered for the ATHP-1 cell line as although the experimental procedure for the accumulation is unaltered differentiation from monocyte to MDM (ATHP-1) cells must occur before the protocol is used. In brief, THP-1 cells, containing phorbol-12-myristate 13 acetate (PMA: Sigma; Dorest, Uk) to final concentration of 10 nM in medium (RPMI-1640 supplemented with 10% FBS) were seeded at a density of approximately 4×10$^6$ cells per well on a 6 well plate. Cells were then incubated at 37° C. and 5% $CO_2$ for 7 days prior to use to allow differentiation to macrophage like cells. Cellular accumulation of nano dispersed drug was quantified as previously described for Caco-2 and HepG2 cell lines.

Cellular Accumulation of Nano Dispersed Lopinavir Compared to their Parental, Aqueous Compounds in Non-Adherent Cells; THP-1 and CEM.

Cellular accumulation was ascertained for each nano-dispersion in THP-1 and CEM cell lines as follows. In brief, cells were harvested at a density of 5×10$^6$ cells per well. Each well was washed ×2 with pre-warmed HBSS (37° C.). To each well, 600 µl of HBSS containing 10 µM lopinavir, each with 0.1 µCi of 3H/14C/3H labelled drug respectively. After incubation for 1 hr the cells are pelleted by centrifugation (2K rpm, 5 min). After 1 hr, an extracellular sample was taken from supernatant (100 µl and added into a 5 ml scintillation vial (Meridian Biotechnologies Ltd; Uk). The supernatant containing drug was aspirated from the well and cells washed ×2 in ice cold HBSS. The ice cold HBSS was aspirated and the addition of 100 µl of tap water to lyse the cells. The 100 µl of cell lysate is then transferred to a 5 ml scintillation vial (Meridian Biotechnologies Ltd; Uk), to each 4 ml of Ultima Gold scintillation fluid was added and scintillation level quantified using a Perkin Elmer 3100TS scintillation counter. Each nano-dispersion was tested in duplicate and scintillation measurements taken in triplicate.

Figure 9:
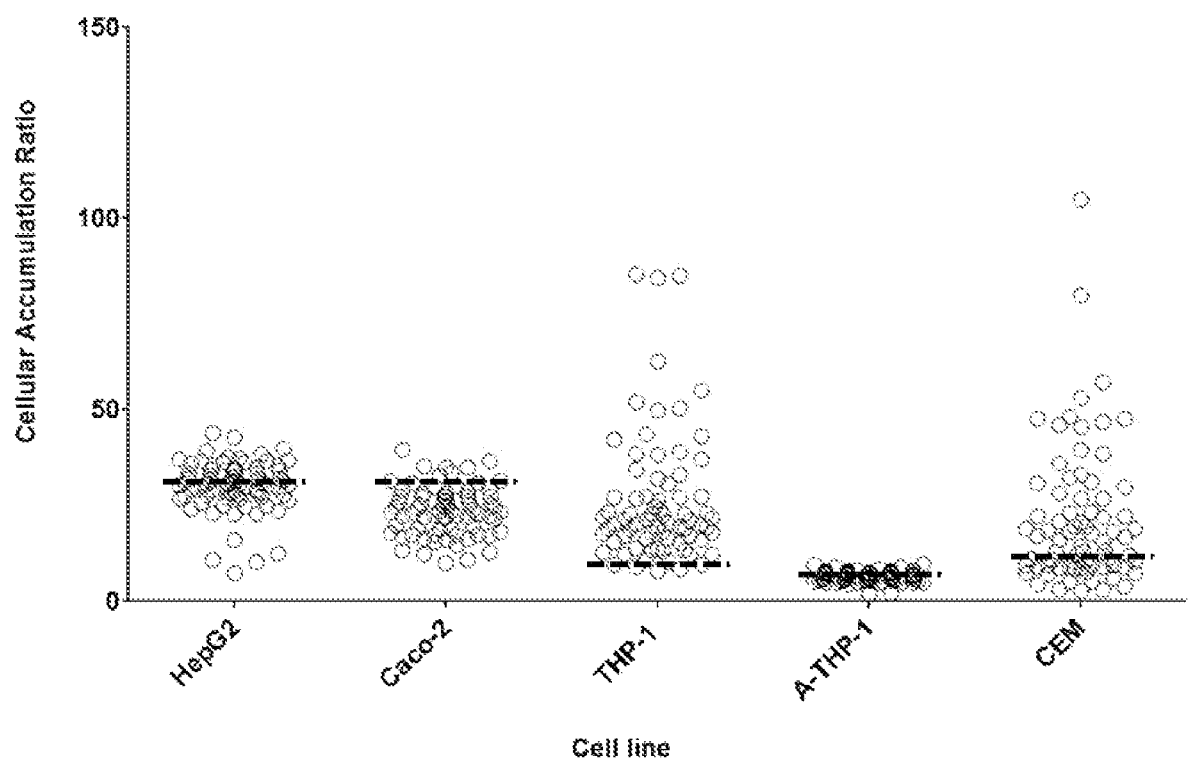
FIG. 9 shows cellular accumulation of 10% lopinavir loaded nanodispersions across various cell lines. Data for aqueous lopinavir are given as dotted horizontal lines.
Figure 10:
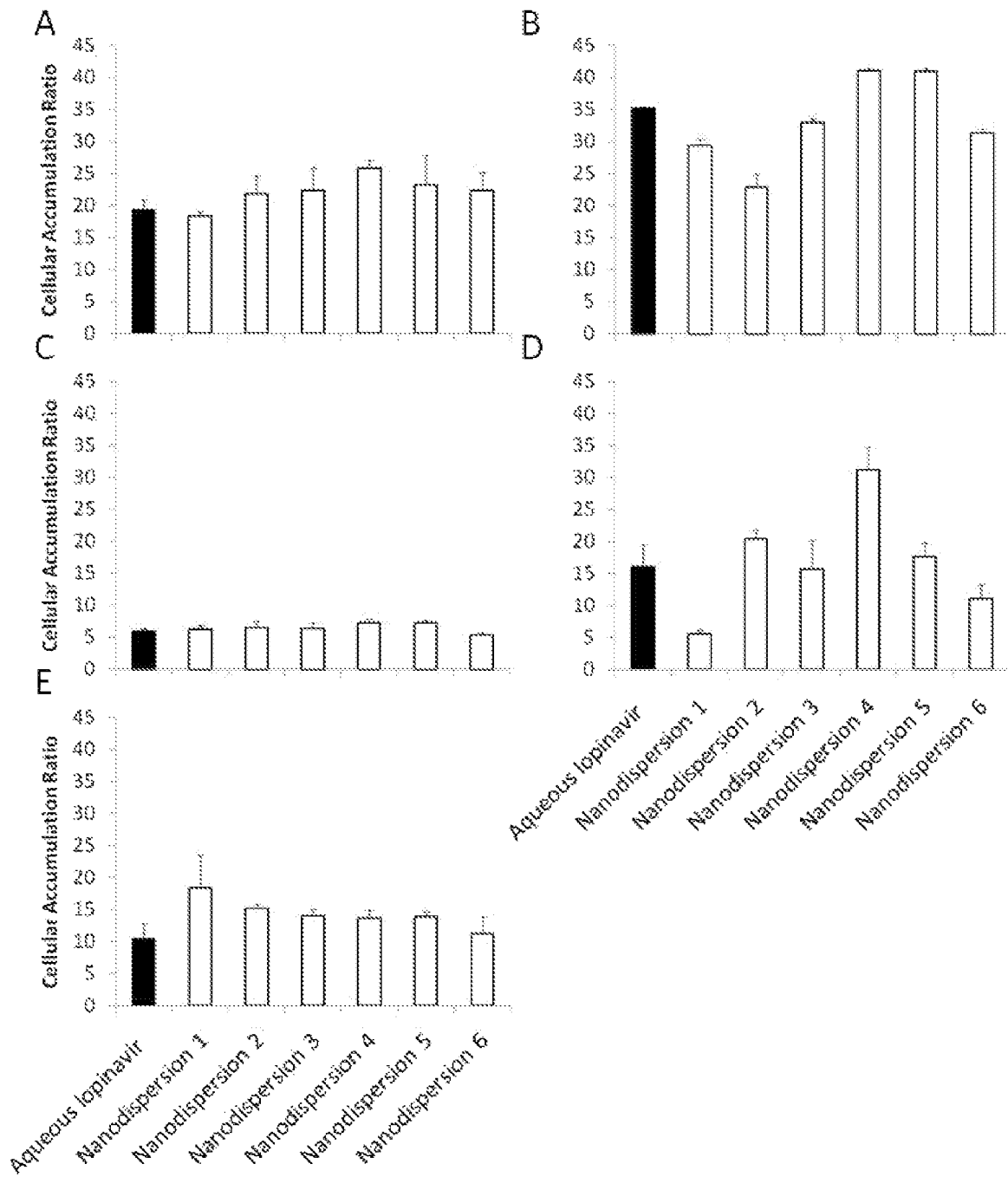
FIG. 10 shows cellular accumulation of 70% lopinavir loaded nanodispersions across various cell lines. Data for aqueous lopinavir are given as dotted horizontal lines. (A) HepG2, (B) Caco-2, (C) THP-1, (D) A-THP-1, (E) CEM.

FIG. 9 shows cellular accumulation ratio (cell-associated drug divided by extracellular drug) of all 10% loaded lopinavir nanodispersions in the studied cell lines. FIG. 10 shows cellular accumulation ratio (cell-associated drug divided by extracellular drug) of 70% loaded lopinavir nanodispersions in the studied cell lines. with respect to the six nanodispersed lopinavir formulations (detailed in Table 7 above) and the parental aqueous drug (i.e. non-nanodispersed) sample described in the present example.

In summary, 10% loaded nanodispersions which exhibit higher cellular penetration into all cell types studied have been synthesised and characterised. In addition, 70% loaded nanodispersions with favourable penetration into these cell types (particularly immune cells) have been identified.

Example 11—Transcellular Permeability of Lopinavir Nanodispersions Across Caco-2 Cell Monolayers For transcellular permeability studies to identify 10% and 70% drug loaded nanodispersion candidates, modelling systemic circulation uptake, Caco-2 cells were propagated to a monolayer over a 21 day period, yielding transepithelial electrical resistance (TER) values of ~1300Ω. For evaluation of 10% loaded nanoparticles, 10 µM of parental or nanoformulated drug (including 0.1 µCi radio-labelled drug) was added to the apical chamber and samples taken at 1 and 2 hr from the basolateral chamber. Each nano dispersed drug was tested in duplicate. For evaluation of 70% loaded nanodispersions, 10 µM of parental or nanoformulated drug (including 0.1 µCi radio-labelled drug) was added to the apical chamber of 4 wells and the basolateral chamber of 4 wells to quantify transport in both apical to basolateral and basolateral to apical direction and sampled on an hourly basis over a 4 h time period. Apparent permeability coefficient was determined by the amount of compound transported using the following equation: Papp=(dQ/dt)(1/(AC$_0$). Where (dQ/dt) is the amount per time (nmol·sec$^{-1}$), A is the surface area of the filter and $C_0$ is the starting concentration of the donor chamber (10 µM).

Figure 11:
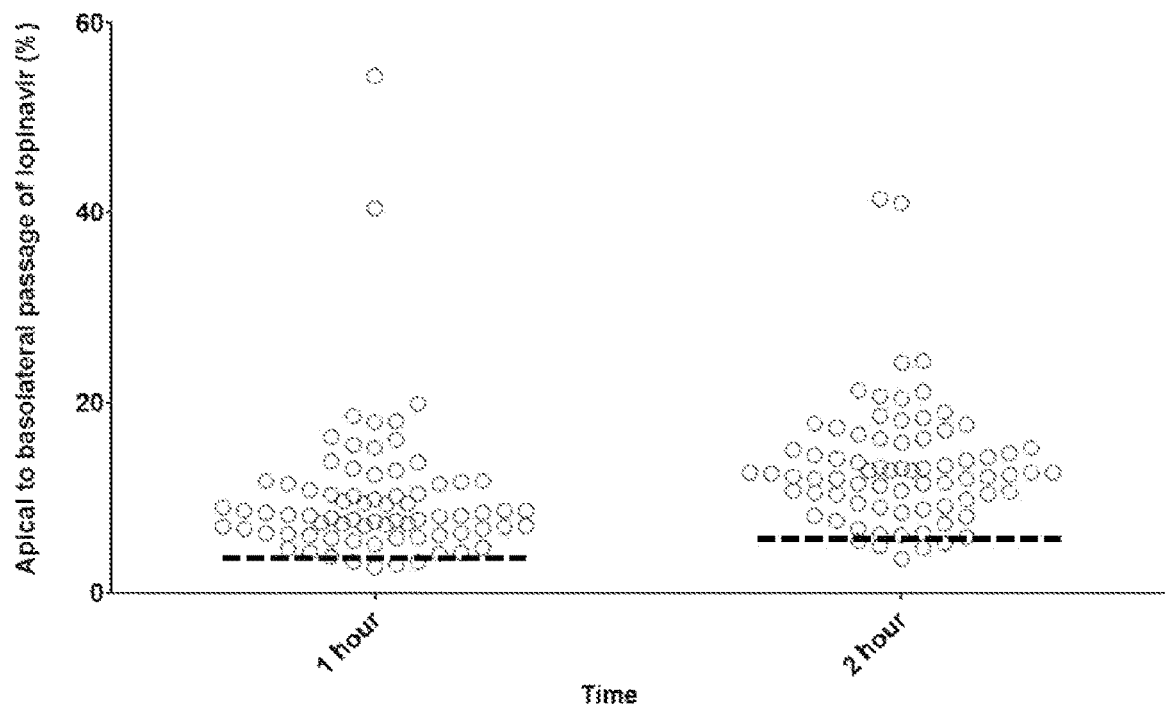
FIG. 11 shows transcellular permeability of 10% lopinavir loaded nanodispersions across Caco-2 cell monolayers. Data for aqueous lopinavir are given as dotted horizontal lines.
Figure 12:
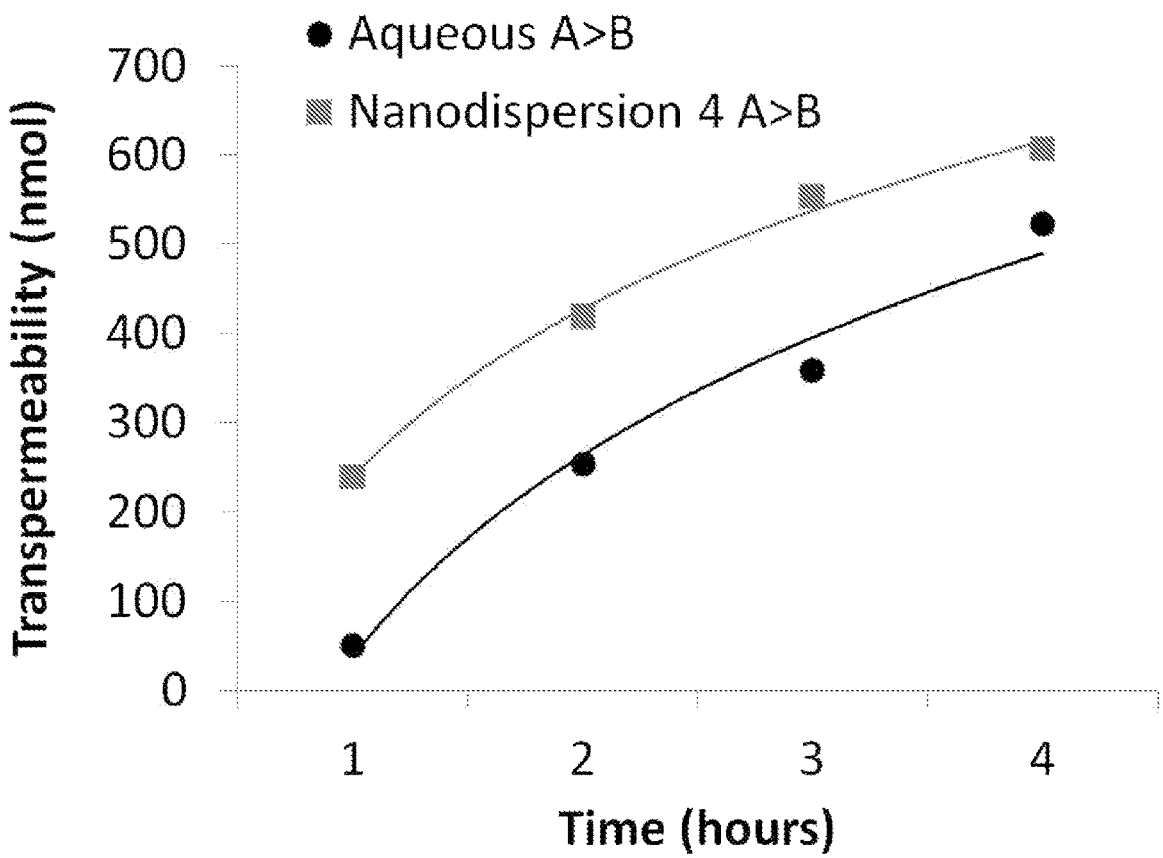
FIG. 12 shows transcellular permeability of 70% lopinavir loaded nanodispersions across Caco-2 cell monolayers relative to aqueous lopinavir. Data are given for apical (gut side) to basolateral (blood side) passage of drug.

FIG. 11 shows apical (gut compartment) to basolateral (blood compartment) transcellular permeability of 10% loaded lopinavir nanodispersions in the studied cell lines. FIG. 12 shows apical to basolateral permeability of 70% loaded lopinavir nanodispersions.

Example 12—Pharmacokinetics of Lopinavir in Rodents Administered a Nanodispersion Versus a Conventional Formulation Adult male Wistar rats, (250-350 g) were terminally anesthetized with 14% urethane in 0.9% saline (1 ml/100 g body weight i.p) and cannulated via the trachea and carotid artery. A pre dose blood sample 0.1 ml was collected into a heparinised Eppendorf vial and centrifuged at 10,000 rpm for 5 minutes, the plasma layer was then removed and stored at −20 C. Rats were then orally dosed with lopinavir, lopinavir/ritonavir or a lopinavir nanodispersion using a 7 cm curved gavarge needle 0.1 ml blood samples were collected via the carotid cannula at the following time points 20', 30', 45', 60', 90', 120', 180', 240', 300'. At the end of the experiment animals were killed using excess of anesthetic. 200 µl of a 30% Hydrogen peroxide (Sigma-Aldrich, Uk) solution was added to each sample and left for 60 minutes. Finally, 30 µl of glacial acetic acid was added and the entire sample incubated for a further 15 minutes at 50° C. 4 ml of Ultima Gold (PerkinElmer, Uk) scintillation fluid was added, sample mixed vigorously, and the dpm was counted using a 3100 TR liquid scintillation counter (IsoTech, Uk). Plasma concentrations of lopinavir were then calculated from the dpm.

Figure 13:
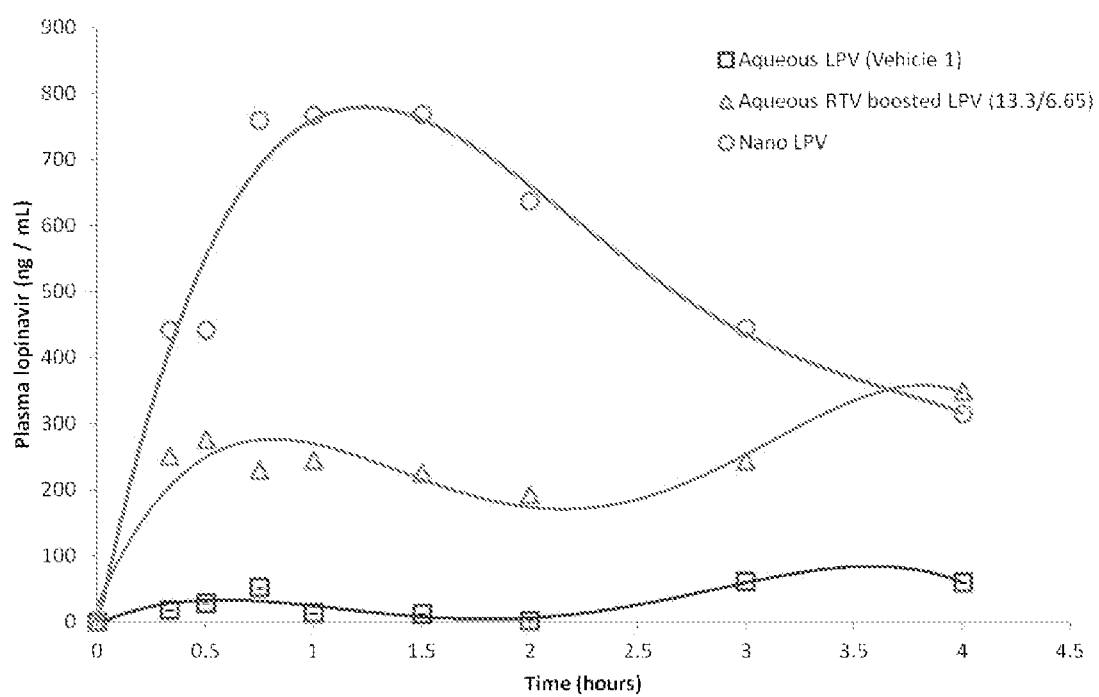
FIG. 13 shows the pharmacokinetics of 70%-loaded lopinavir nanodispersions after oral administration to rats relative to rats orally dosed with conventional formulations of either lopinavir alone or lopinavir/ritonavir. The figure shows lopinavir plasma levels over time with aqueous lopinavir (squares); aqueous ritonavir-boosted lopinavir (triangles); and nanoparticles of lopinavir (circles).

FIG. 13 shows pharmacokinetics of lopinavir, lopinavir/ritonavir and 70%-loaded lopinavir nanodispersion (without ritonavir) in rats. A demonstrably higher plasma lopinavir concentration was seen for the nanodispersion than for either lopinavir alone or lopinavir/ritonavir.

CONCLUSION

The lopinavir formulations of the present invention are hereby shown to form stable nanodispersions with a number of favourable pharmacological properties. Nanodispersions have been synthesised that have lower cytotoxicity, that exhibit more potent inhibition of HIV protease, that exhibit more potent inhibition of HIV replication, that accumulate to a higher degree in HIV target cells and that traverse intestinal epithelial cells more rapidly and more completely than aqueous solutions of lopinavir. Furthermore, nanodispersions of lopinavir with favourable pharmacokinetic properties relative to conventional formulation have been generated.

What is claimed is:

1. A solid lopinavir composition, comprising nanoparticles of lopinavir dispersed within a solid mixture of at least one hydrophilic polymer and at least one surfactant;
   wherein the hydrophilic polymer is polyvinyl alcohol (PVA) and the surfactant is vitamin-E-polyethylene glycol-succinate (Vit-E-PEG-succinate) and
   wherein the solid composition comprises:
   40-80 wt % lopinavir;
   10 to 40 wt % PVA; and
   2 to 20 wt % Vit-E-PEG-succinate.

2. A solid lopinavir composition according to claim 1, wherein the nanoparticles of lopinavir have an average particle size of less than or equal to 1 micron (µm).

3. A solid lopinavir composition according to claim 2, wherein the nanoparticles of lopinavir have an average particle size between 100 and 800 nm.

4. A solid lopinavir composition according to claim 1, wherein the polydispersity of the nanoparticles of lopinavir is less than or equal to 0.8.

5. A solid lopinavir composition according to claim 1 comprising:
   60-80% lopinavir;
   15-25 wt % PVA; and
   5-15 wt % vitamin-E-polyethylene glycol-succinate (Vit-E-PEG-succinate).

6. A pharmaceutical composition in a solid dosage form comprising a solid composition according to claim 1, and optionally one or more additional pharmaceutically acceptable excipients.

7. A process for preparing a solid composition according to claim 1, the process comprising:
   preparing an oil in water emulsion comprising:
   an oil phase comprising lopinavir; and
   an aqueous phase comprising a hydrophilic polymer and a surfactant, each as defined in claim 1; and
   removing the oil and water to form the solid composition.

8. A process for preparing a solid composition according to claim 1, the process comprising:
   preparing a single phase solution comprising lopinavir, a hydrophilic polymer as defined in claim 1, and a surfactant as defined in claim 1, in one or more solvents; and spray-drying the mixture to remove the one or more solvents to form the solid composition.

9. A method of treating an HIV retroviral infection, the method comprising administering a therapeutically effective amount of a solid composition according to claim 1, or a pharmaceutical composition according to claim 6 to a patient suffering from the HIV retroviral infection.

10. A method of treating an HIV retroviral infection, said method comprising the step of administering a therapeutically effective amount of a solid composition according to claim 1, or a pharmaceutical composition according to claim 6, in combination with one or more other antiretroviral agents, to a patient suffering from the HIV retroviral infection.

* * * * *